US012714759B2

(12) United States Patent
Shively et al.

(10) Patent No.: US 12,714,759 B2
(45) Date of Patent: Aug. 25, 2026

(54) COMBINATION THERAPY FOR TREATING CANCER

(71) Applicant: City of Hope, Duarte, CA (US)

(72) Inventors: John E. Shively, Arcadia, CA (US); Maciej Kujawski, Glendora, CA (US); Megan Minnix, Monrovia, CA (US); Paul Yazaki, Glendale, CA (US)

(73) Assignee: CITY OF HOPE, Duarte, CA (US)

( * ) Notice: Subject to any disclaimer, the term of this patent is extended or adjusted under 35 U.S.C. 154(b) by 796 days.

(21) Appl. No.: 18/145,614

(22) Filed: Dec. 22, 2022

(65) Prior Publication Data

US 2023/0256122 A1 Aug. 17, 2023

Related U.S. Application Data

(60) Provisional application No. 63/294,249, filed on Dec. 28, 2021.

(51) Int. Cl.

*A61K 51/10* (2006.01)
*A61K 47/68* (2017.01)
*A61P 35/00* (2006.01)

(52) U.S. Cl.

CPC ...... *A61K 51/1048* (2013.01); *A61K 47/6813* (2017.08); *A61K 47/6853* (2017.08); *A61K 51/1096* (2013.01); *A61P 35/00* (2018.01)

(58) Field of Classification Search

CPC ............ A61K 51/1048; A61K 47/6813; A61K 47/6853; A61K 51/1096; A61K 51/1093; A61P 35/00

See application file for complete search history.

(56) References Cited

U.S. PATENT DOCUMENTS 7,273,608 B2 9/2007 Yazaki et al.
8,603,479 B1 * 12/2013 Hansen .................. C07K 14/54 530/387.3

FOREIGN PATENT DOCUMENTS

WO WO-91/01990 A1 2/1991
WO WO-93/25237 A1 12/1993

OTHER PUBLICATIONS

Akhavan, D. et al. (Feb. 2020, e-published Jan. 7, 2020). "Phase I Study of Yttrium-90 Radiolabeled M5A Anti-Carcinoembryonic Antigen Humanized Antibody in Patients with Advanced Carcinoembryonic Antigen Producing Malignancies," *Cancer Biotherapy and Radiopharmaceuticals* 35(1):10-15.

Brechbiel, M.W. (Jun. 2008, e-published Nov. 28, 2007). "Bifunctional chelates for metal nuclides," *Q J Nucl Med Mol Imaging* 52(2):166-173.

Chen, Y. et al. (Jul. 28, 2020). "SBRT combined with PD-1/PD-L1 inhibitors in NSCLC treatment: a focus on the mechanisms, advances, and future challenges," *Journal of Hematology & Oncology* 13(1):105.

Johannsen, M. et al. (Nov. 2010, e-published Aug. 24, 2010). "The tumour-targeting human L19-IL2 immunocytokine: preclinical safety studies, phase I clinical trial in patients with solid tumours and expansion into patients with advanced renal cell carcinoma," *European Journal of Cancer* 46(16):2926-2935.

Kujawski, M. et al. (Feb. 14, 2020). "Potent immunomodulatory effects of an anti-CEA-IL-2 immunocytokine on tumor therapy and effects of stereotactic radiation," *Oncoimmunology* 9(1):e1724052.

Lewis, M.R. et al. (Nov-Dec. 1994). "A facile, water-soluble method for modification of proteins with DOTA. Use of elevated temperature and optimized pH to achieve high specific activity and high chelate stability in radiolabeled immunoconjugates," *Bioconjugate Chem* 5(6):565-576.

List, T. et al. (Aug. 20, 2013). "Immunocytokines: a review of molecules in clinical development for cancer therapy," *Clinical Pharmacology* 5(Suppl 1):29-45.

Liu, Y. et al. (2010). "A Brief Review of Chelators for Radiolabeling Oligomers," *Materials* 3:3204-3217.

Minnix, M. et al. (Dec. 2022, e-published Jun. 30, 2022). "Improved tumor responses with sequential targeted a followed by Interleukin IL2 immunocytokine therapies in treatment of CEA positive breast and colon tumors in CEA transgenic mice," *Journal of Nuclear Medicine* 40 pages.

Minnix, M. et al. (Jan. 2021, e-published Jul. 3, 2020). "TAG-72-Targeted α-Radionuclide Therapy of Ovarian Cancer Using $^{225}$Ac-Labeled DOTAylated-huCC49 Antibody," The Journal of Nuclear Medicine 62(1):55-61.

Otto, M. et al. (Dec. 1, 2005). "Combination immunotherapy with clinical-scale enriched human gammadelta T cells, hu14.18 antibody, and the immunocytokine Fc-IL7 in disseminated neuroblastoma," *Clin Cancer Res* 11(23):8486-8491.

Poty, S. et al. (Jun. 2018, e-published Mar. 15, 2018). "α-Emitters for Radiotherapy: From Basic Radiochemistry to Clinical Studies—Part 1," *The Journal of Nuclear Medicine* 59(6):878-884.

Sahlmann, C-O. et al. (Feb. 15, 2017, e-published Oct. 20, 2016). "Repeated Adjuvant Anti-CEA Radioimmunotherapy After Resection of Colorectal Liver Metastases: Safety, Feasibility, and Long-Term Efficacy Results of a Prospective Phase 2 Study," *Cancer* 123(4):638-649.

Sta Maria, N.S. et al. (Nov. 10, 2015). "Low Dose Focused Ultrasound Induces Enhanced Tumor Accumulation of Natural Killer Cells," *PLOS One* 10(11):e0142767.

Wardman, P. (Aug. 2007, e-published May 2, 2007). "Chemical radiosensitizers for use in radiotherapy," *Clinical Oncology* 19:397-417.

Xu, X. et al. (Aug. 15, 2000). "Targeting and therapy of carcinoembryonic antigen-expressing tumors in transgenic mice with an antibody-interleukin 2 fusion protein," *Cancer Research* 60(16):4475-4484.

(Continued)

*Primary Examiner* — Robert S Cabral

(74) *Attorney, Agent, or Firm* — Mintz, Levin, Cohn, Ferris, Glovsky and Popeo, P.C.

(57) ABSTRACT

Provided herein, inter alia, are radionuclide-labeled antibodies, immunocytokines, and methods for treating cancer using combination therapy with the radionuclide-labeled antibodies and the immunocytokines.

20 Claims, 20 Drawing Sheets

Specification includes a Sequence Listing.

(56) References Cited

OTHER PUBLICATIONS

Yang, H. et al. (Jan. 2022, e-published Sep. 9, 2021). "Harnessing α-emitting radionuclides for therapy-radiolabeling method review," *J Nucl Med* 63(1):5-13.
Yazaki, P.J. et al. (Feb. 2008). "Biodistribution and tumor imaging of an anti-CEA single-chain antibody-albumin fusion protein," *Nucl Med Biol* 35(2):151-158.
Yazaki, P.J. et al. (May 2004, e-published Aug. 17, 2004). "Humanization of the anti-CEA T84.66 antibody based on crystal structure data," *Protein Eng Des Sel* 17(5):481-489.

* cited by examiner

FIG. 2D
Spleen
TDLN
Tumor
0
20
40
60
80
Saline
TAT
ICK
ICK+TAT
TAT+ICK
FIG. 2E
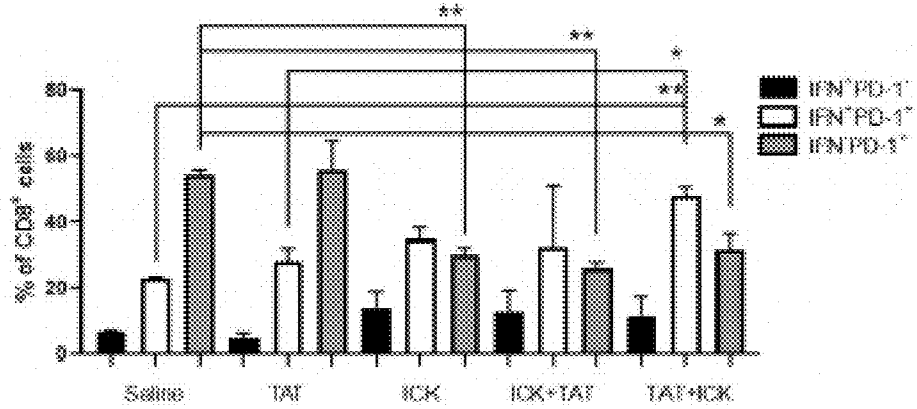
FIG. 2F
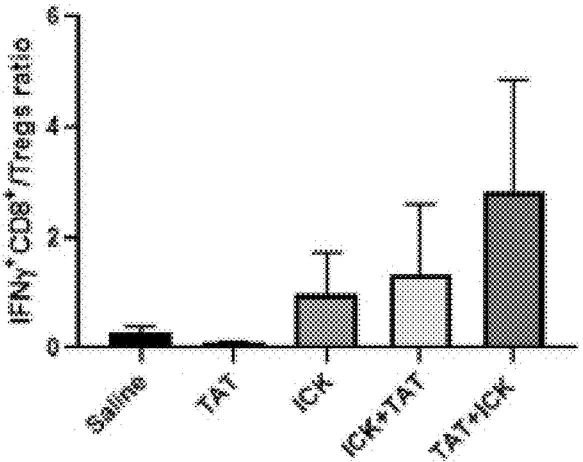

Saline
7.4 kBq $^{225}$Ac-M5A
ICK Alone
7.4 kBq $^{225}$Ac-M5A + ICK (13d)
7.4 kBq $^{225}$Ac-M5A + ICK (18d)

FIG. 5C
FIG. 5D
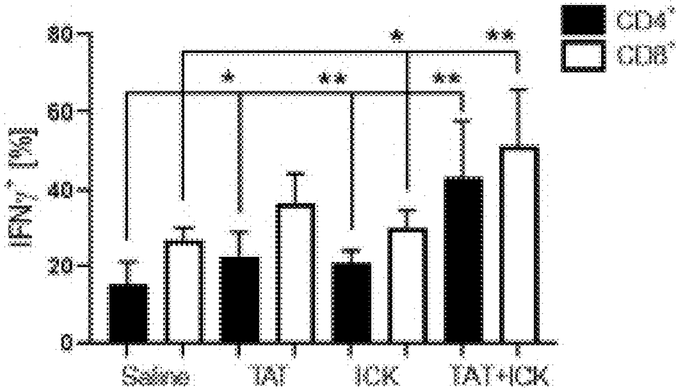
FIG. 5E
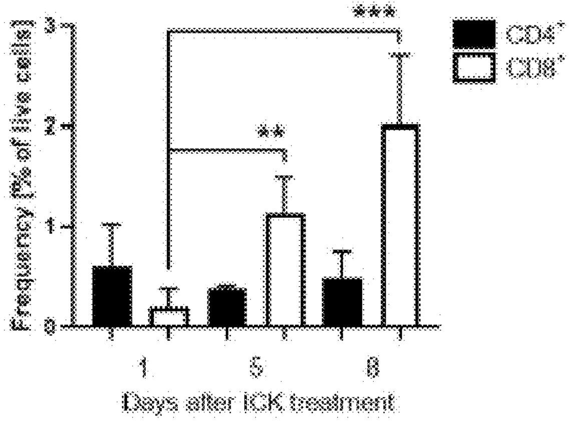

COMBINATION THERAPY FOR TREATING CANCER

CROSS-REFERENCE TO RELATED APPLICATIONS

This application claims the benefit of priority to U.S. Application No. 63/294,249 filed Dec. 28, 2021, the disclosure of which is incorporated by reference herein in its entirety.

REFERENCE TO A "SEQUENCE LISTING," A TABLE, OR A COMPUTER PROGRAM LISTING APPENDIX SUBMITTED AS AN ASCII FILE

The Sequence Listing written in file 048440-804001US_Sequence_Listing, created Dec. 21, 2022, with 13,396 bytes, machine format IBM-PC, MS Windows operating system, is hereby incorporated by reference.

BACKGROUND

Carcinoembryonic antigen (CEA, CEACAM5) is a pan-carcinoma antigen that is highly expressed in colon, breast, pancreatic, and lung cancers. (Refs 1-4). CEA is an apical GPI-linked cell surface antigen that, in the case of tumor expression, is released into the circulation. (Ref 5) Accordingly, detection of serum levels of CEA in patients is used to monitor cancer progression. (Refs 6-8) Since there are a large number of homologous members of the CEA gene family, many of which are expressed in normal tissue, the selection of a CEA-specific antibody is critical to the detection of CEA positive malignancies. (Refs 5, 9). Radiolabeled CEA specific antibodies have been used to image a variety of CEA expressing tumors, confirming their in vivo specificity. (Refs 10-12). Since most anti-CEA antibodies are not cytotoxic, they require the conjugation of drugs or radionuclides to be therapeutic. In this respect radioimmunotherapy (RIT) with anti-CEA antibodies radiolabeled with the beta-emitters $^{131}$I or $^{90}$Y have met with some success in the clinic. (Refs. 13-17). In the case of immunotherapy, a phase 1 trial with a bispecific antibody targeting CEA on tumor cells and CD3 on T cells combined with atezolizumab in metastatic colorectal cancer, 21.5% of patients had a partial response and 36% of patients had a 10-30% reduction in tumors. (Ref. 18). There are also several clinical trials (NCT04513431, NCT04348643, NCT02349724) investigating CAR T cell therapy targeting CEA, with mixed results. (Ref 19). There is a need in the art for new cancer therapies, and the present disclosure is directed to this need.

BRIEF SUMMARY

Provided herein are humanized anti-carcinoembryonic antigen (CEA) antibodies bonded to alpha-emitting radionuclides. In embodiments, the humanized anti-CEA antibody is covalently bonded to a chelating agent and the chelating agent is complexed with the alpha-emitting radionuclide.

Provided herein are methods of treating cancer in a subject in need thereof by administering to the subject an effective amount of a first anti-carcinoembryonic antigen (CEA) antibody bonded to an alpha-emitting radionuclide, and an effective amount of an immunocytokine comprising a second anti-carcinoembryonic antigen (CEA) antibody covalently bonded to a cytokine; wherein the immunocytokine is administered to the subject after the first anti-CEA antibody is administered to the subject. In embodiments, the first anti-CEA antibody is covalently bonded to a chelating agent and the chelating agent is complexed with the alpha-emitting radionuclide. In embodiments, the first anti-CEA antibody and the second anti-CEA antibody are humanized anti-CEA antibodies.

These and other embodiments of the disclosure are described in detail herein.

BRIEF DESCRIPTION OF THE DRAWINGS

FIG. 1A: Tumor growth curves (3.7 kBq $^{225}$Ac-M5A, p=0.84; 7.4 kBq $^{225}$Ac-M5A, p=0.06; 11.1 kBq $^{225}$Ac-M5A, p=0.005). FIG. 1B: Kaplan-Meier survival plot (3.7 kBq $^{225}$Ac-M5A, p=0.03; 7.4 kBq $^{225}$Ac-M5A, p=0.007; 11.1 kBq $^{225}$Ac-M5A, p=0.007). FIG. 1C: Percent weight loss vs days post E0771/CEA injection (3.7 kBq $^{225}$Ac-M5A, p=0.18; 7.4 kBq $^{225}$Ac-M5A, p=0.99; 11.1 kBq $^{225}$Ac-M5A, p=0.42). FIG. 1D: Flow cytometry analysis of the blood indicates significant decrease of CD8 T-cells and B cells for two highest doses of TAT. FIG. 1E: The highest dose of TAT significantly reduces tumor infiltration of CD4 and CD8 T-cells, analyzed by flow cytometry. FIG. 1F: Increase of tumor infiltrating neutrophils induced by 7.4 kBq and 11.1 kBq TAT, analyzed by flow cytometry. *p<0.001; p<0.01; *p<0.05. Arrow=TAT given at day 8. N=4. N-value and graphs do not include the 2 mice/group that were euthanized at 21 days for flow analysis.

FIGS. 2A-2F are directed to experiments determining the order of 7.4 kBq $^{225}$Ac-M5A (TAT) and ICK combination therapy in orthotopic breast carcinoma model. All treatments were started on day 8 post E0771/CEA injection, either 7.4 kBq TAT or four doses of ICK, given once daily for four days at 1 mg/kg. In the combination groups, ICK+TAT, TAT was given on day 13 and in the TAT+ICK group, the ICK regimen was started 10 days post TAT (18d). FIG. 2A: Tumor growth curves (TAT, p=0.13; ICK, p=0.02; ICK+TAT, p=0.07; TAT+ICK, p=0.02). FIG. 2B: Kaplan-Meier survival plot (TAT, p=0.007; ICK, p=0.02; ICK+TAT, p=0.00$^7$; TAT+ICK, p=0.007) FIG. 2C: TAT therapy alone or in combination TAT+ICK affects viability of treated tumors at day 21, shown by flow cytometry. FIG. 2D: Significant increase of tumor infiltrating IFNγ$^+$CD8$^+$ T-cells in mice treated with TAT+ICK at day 21, analyzed by intracellular flow cytometry. FIG. 2E: Increase of IFNγ/PD-1 double-positive tumor infiltrating CD8$^+$ T-cells in mice treated with TAT+ICK at day 21, analyzed by intracellular flow cytometry. FIG. 2F: TAT+ICK combination changes the ration of IFNγ+CD8$^+$ T-cells to regulatory T-cells in tumor tissue, analyzed by intracellular flow cytometry. *p<0.001; p<0.01; *p<0.05. N=4. N-value and graphs do not include the 2 mice/group that were euthanized at 21 days for flow analysis.

FIG. 3A: Tumor growth curves (TAT, p=0.10; ICK, p=0.06; TAT+ICK(13 days), p=0.02; TAT+ICK(18 days), p=0.03). FIG. 3B: Kaplan-Meier survival plot (TAT, p=0.01; ICK, p=0.01; TAT+ICK(13 days), p=0.002; TAT+ICK(18 days), p=0.002). FIG. 3C: Combination of TAT and ICK given at day 13 or 18 affects viability of treated tumors at day 21, shown by flow cytometry. FIG. 3D: Significant decrease of tumor infiltrating Tregs in mice treated with TAT and ICK given at day 13 or 18, analyzed by intracellular flow cytometry at day 21. FIG. 3E: TAT and ICK given at day 13 or 18 increases tumor infiltration of IFNγ+$CD8^+$ T-cells, analyzed by intracellular flow cytometry at day 21. FIG. 3F: TAT and ICK given at day 13 or 18 changes the ration of IFNγ+$CD8^+$ T-cells to regulatory T-cells in tumor tissue, analyzed by intracellular flow cytometry. *p<0.001; p<0.01; *p<0.05. Sal N=3, TAT or ICK alone N=4, Combination therapy N=6. N-value and graphs do not include the 2 mice/group that were euthanized at 21 days for flow analysis.

FIG. 4A: Tumor growth curves (3.7 kBq $^{225}$Ac-M5A, p=0.98; 7.4 kBq $^{225}$Ac-M5A, p=0.16; 11.1 kBq $^{225}$Ac-M5A, p=0.14). FIG. 4B: Kaplan-Meier survival plot (3.7 kBq $^{225}$Ac-M5A, p=0.37; 7.4 kBq $^{225}$Ac-M5A, p=0.007; 11.1 kBq $^{225}$Ac-M5A, p=0.007) Red arrow=TAT given at day 13. N=4. FIG. 4C: Tumor growth curves for each replicate (7.4 kBq×2 TAT, p=0.009; 14.8 kBq TAT, p=0.0007) FIG. 4D: Kaplan-Meier survival plot (7.4 kBqx2 TAT, p=0.002; 14.8 kBq TAT, p=0.001) N=5-6.

FIGS. 5A-5G show combination therapy of 7.4 kBq $^{225}$Ac-M5A followed by ICK. TAT was given day 13 post MC38/CEA injection, followed by ICK treatment starting on day 23. FIG. 5A: Tumor growth curves (TAT, p=0.003; ICK, p=0.01; TAT+ICK, p=0.0002). FIG. 5B: Kaplan-Meier survival plot (TAT, p=0.0001; ICK, p=0.001; TAT+ICK, p=0.0001). ICK alone N=5; Saline, TAT alone and Combination therapy N=7. FIG. 5C: Significant increase of tumor infiltrating CD4+ and $CD8^+$ T-cells in mice treated with ICK, analyzed by flow cytometry at day 27. FIG. 5D: Significant increase of tumor infiltrating IFN$\gamma^+$ $CD4^+$ and $CD8^+$ T-cells in mice treated with ICK or TAT+ ICK, analyzed by intracellular flow cytometry at day 27. FIG. 5E: Tumors analyzed at day 1, 5 and 8 after last dose of ICK in TAT+ICK group shows gradual increase of $CD8^+$ T-cells infiltration, analyzed by flow cytometry. FIG. 5F: Increase of tumor infiltrating IFN$\gamma^+$$CD8^+$ T-cells at day 5 and 8 after last dose of ICK in TAT+ICK group, analyzed by intracellular flow cytometry. FIG. 5G: Change in the ration of IFN$\gamma^+$$CD8^+$ T-cells to regulatory T-cells in tumor tissue at day 5 and 8 after last dose of ICK in TAT+ICK group, analyzed by intracellular flow cytometry. * p<0.001; p<0.01; *p<0.05.

FIGS. 6A-6D: in the orthotopic mammary tumor model, vascularity as measured by CD31 staining was most affected by combination therapy as evidenced by increased staining and vessel size especially at the tumor periphery. FIGS. 6E-6H: In the colon cancer model, the vascularity of untreated tumors showed even CD31 staining across the entire tumor that was greatly disrupted by TAT only, ICK only and combination therapies.

FIG. 12A: White Blood Cells (WBC). FIG. 12B: leukocyte counts. FIG. 12C: leukocyte percents. FIG. 12D: Red blood Cells (RBC). FIG. 12D: Platelets.

FIG. 13A: White Blood Cells (WBC). FIG. 13B: leukocytes counts. FIG. 13C: leukocytes percents. FIG. 13D: Red blood Cells (RBC). (FIG. 13E: Platelets.

FIG. 15A: White Blood Cells (WBC). FIG. 15C: leukocyte counts. FIG. 15D: leukocyte percents. FIG. 15D: Red blood Cells (RBC). FIG. 15E: Platelets.

FIG. 16A: White Blood Cells (WBC). FIG. 16B: leukocyte counts. FIG. 16C: leukocyte percents.

Figure 1A:
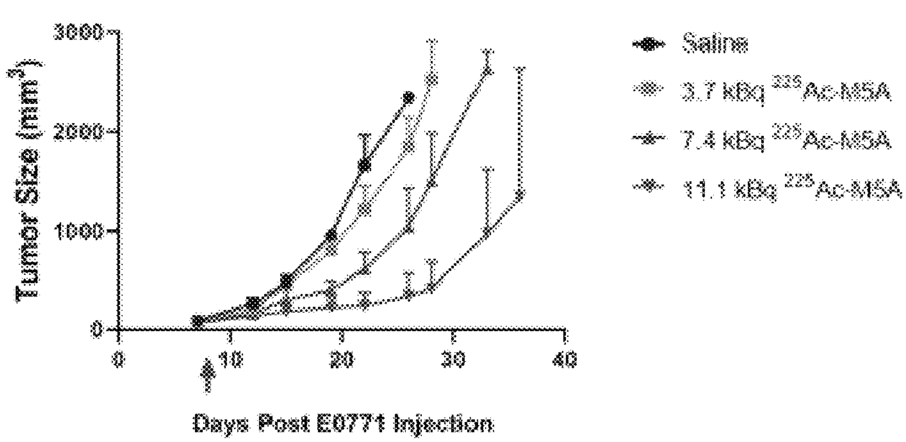
FIGS. 1A-1F show TAT therapy of murine E0771/CEA breast carcinoma in a dose escalation study.
Figure 1B:
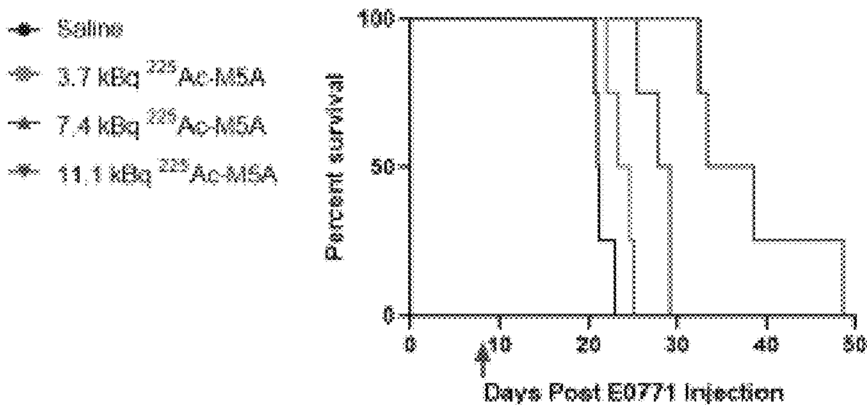

Color versions of certain figures described herein are available in Minnix et al, Journal of Nuclear Medicine, published Jun. 30, 2022, as doi:10.2967/jnumed.122.264126, the disclosure of which is incorporated by reference herein in its entirety.

DETAILED DESCRIPTION

Definitions

Unless defined otherwise, technical and scientific terms used herein have the same meaning as commonly understood by a person of ordinary skill in the art. See, e.g., Singleton et al., Dictionary of Microbiology and Molecular Biology, 2nd ed., J. Wiley & Sons (New York, NY 1994); Sambrook et al., Molecular Cloning, A Laboratory Manual, Cold Springs Harbor Press (Cold Springs Harbor, NY 1989). Any methods, devices and materials similar or equivalent to those described herein can be used in the practice of this disclosure. The following definitions are provided to facilitate understanding of certain terms used frequently herein and are not meant to limit the scope of the present disclosure.

The term "carcinoembryonic antigen" or "CEA" or "carcinoembryonic antigen-related cell adhesion molecule 5" or "CEACAM5" as provided herein includes any of the recombinant or naturally-occurring forms of CEA or variants or homologs thereof that maintain CEA protein activity (e.g., within at least 50%, 80%, 90%, 95%, 96%, 97%, 98%, 99% or 100% activity compared to V CEA). In embodiments, the variants or homologs have at least 90%, 95%, 96%, 97%, 98%, 99% or 100% amino acid sequence identity across the whole sequence or a portion of the sequence (e.g., a 5, 10, 15, or 20 continuous amino acid portion) compared to a naturally occurring CEA protein. In embodiments, CEA is identified by the UniProtKB Reference Number P06731, or a variant, homolog or functional fragment thereof.

The term "anti-carcinoembryonic antigen antibody" or "anti-CEA antibody" refers to an antibody having CDRs that bind to an epitope of CEA.

"M5A" or "M5A antibody" refers to a humanized anti-carcinoembryonic antigen antibody having a CDR-L1 as in SEQ ID NO:1, CDR-L2 as in SEQ ID NO:2, CDR-L3 as in SEQ ID NO:3, CDR-H1 as in SEQ ID NO:4, CDR-H2 as in SEQ ID NO:5, and CDR-H3 as in SEQ ID NO:6, having the variable light chain domain as in SEQ ID NO:8, and having the variable heavy chain domain as in SEQ ID NO:9. M5A is described in U.S. Pat. No. 7,273,608.

"M5B" or "M5B antibody" refers to a humanized anti-carcinoembryonic antigen antibody having a CDR-L1 as in SEQ ID NO:1, CDR-L2 as in SEQ ID NO:2, CDR-L3 as in SEQ ID NO:3, CDR-H1 as in SEQ ID NO:4, CDR-H2 as in SEQ ID NO:7, and CDR-H3 as in SEQ ID NO:6, having the variable light chain domain as in SEQ ID NO:8, and having the variable heavy chain domain as in SEQ ID NO:10. M5B is described in U.S. Pat. No. 7,273,608.

"T84.66" or "T84.66 antibody" refers to an anti-carcinoembryonic antigen antibody having a CDR-L1 as in SEQ ID NO:1, CDR-L2 as in SEQ ID NO:2, CDR-L3 as in SEQ ID NO:3, CDR-H1 as in SEQ ID NO:4, CDR-H2 as in SEQ ID NO:5, and CDR-H3 as in SEQ ID NO:6, having the variable light chain domain as in SEQ ID NO:11, and having the variable heavy chain domain as in SEQ ID NO:12. T84.66 is described in U.S. Pat. No. 7,273,608.

Antibodies are large, complex molecules with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen and a constant ("C") region that interacts with other components of the immune system. The light and heavy chain variable regions come together in 3-dimensional space to form a variable region that binds the antigen. Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The part of a variable region not contained in the CDRs is called the framework ("FR"), which forms the environment for the CDRs. In embodiments, the position of CDRs and FRs are defined herein by the Chothia numbering system (Chothia et al, J. Mol. Biol, 196(4):901-917 (1987); Chothia et al, Nature, 342(6252:877-883 (1989); Al-Lazikani et al, J. Mol. Biol. 273(4):927-948 (1997)). In embodiments, the positions occupied by individual residues within the light or the heavy chain of an antibody are defined herein by the Chothia numbering system. In embodiments, the position of CDRs and FRs are defined herein by the Kabat numbering system (Kabat et al., Sequences of Proteins of Immunological Interest, Fifth Edition, U.S. Department of Health and Human Services, U.S. Government Printing Office (1991)). In embodiments, the positions occupied by individual residues within the light or the heavy chain of an antibody are defined herein by the Kabat numbering system. Throughout this disclosure, the location of residues required for binding within a light chain and a heavy chain of an antibody are defined by the position of the residue according to the Kabat numbering system or the Chothia numbering system, as is well known in the art.

The term "antibody" is used according to its commonly known meaning in the art. Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_{H1}$ by a disulfide bond. The $F(ab)'_2$ may be reduced under mild conditions to break the disulfide linkage in the hinge region, thereby converting the $F(ab)'^2$ dimer into an Fab' monomer. The Fab' monomer is essentially Fab with part of the hinge region (see Fundamental Immunology (Paul ed., 3d ed. 1993)). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

An "antibody variant" as provided herein refers to a polypeptide capable of binding to an antigen and including one or more structural domains of an antibody or fragment thereof. Non-limiting examples of antibody variants include single-domain antibodies or nanobodies, affibodies (polypeptides smaller than monoclonal antibodies and capable of binding antigens with high affinity and imitating monoclonal antibodies, monospecific $Fab_2$, bispecific $Fab_2$, trispecific $Fab_3$, monovalent IgGs, scFv, bispecific diabodies, trispecific triabodies, scFv-Fc, minibodies, IgNAR, V-NAR, hcIgG, VhH, or peptibodies. A "nanobody" or "single domain antibody" as described herein is commonly well known in the art and refers to an antibody fragment consisting of a single monomeric variable antibody domain. Like a whole antibody, it is able to bind selectively to a specific antigen.

The terms "CDR L1", "CDR L2" and "CDR L3" as provided herein refer to the complementarity determining regions (CDR) 1, 2, and 3 of the variable light (L) chain of an antibody. In embodiments, the variable light chain provided herein includes in N-terminal to C-terminal direction a CDR L1, a CDR L2 and a CDR L3. Likewise, the terms "CDR H1", "CDR 112" and "CDR H3" as provided herein refer to the complementarity determining regions (CDR) 1, 2, and 3 of the variable heavy (H) chain of an antibody. In embodiments, the variable heavy chain provided herein includes in N-terminal to C-terminal direction a CDR H1, a CDR H2 and a CDR H3.

The terms "FR L1", "FR L2", "FR L3" and "FR L4" as provided herein are used according to their common meaning in the art and refer to the framework regions (FR) 1, 2, 3 and 4 of the variable light (L) chain of an antibody. In embodiments, the variable light chain provided herein includes in N-terminal to C-terminal direction a FR L1, a FR L2, a FR L3 and a FR L4. Likewise, the terms "FR H1", "FR 112", "FR H3" and "FR 114" as provided herein are used according to their common meaning in the art and refer to the framework regions (FR) 1, 2, 3 and 4 of the variable heavy (H) chain of an antibody. In embodiments, the variable heavy chain provided herein includes in N-terminal to C-terminal direction a FR H1, a FR H2, a FR H3 and a FR H4.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL), variable light chain (VL) domain, or light chain variable region and variable heavy chain (VH), variable heavy chain (VH) domain, or heavy chain variable region refer to these light and heavy chain regions, respectively. The terms variable light chain (VL), variable light chain (VL) domain, and light chain variable region as referred to herein may be used interchangeably. The terms variable heavy chain (VH), variable heavy chain (VH) domain, and heavy chain variable region as referred to herein may be used interchangeably. The Fc (i.e. fragment crystallizable region) is the "base" or "tail" of an immunoglobulin and is typically composed of two heavy chains that contribute two or three constant domains depending on the class of the antibody. By binding to specific proteins, the Fc region ensures that each antibody generates an appropriate immune response for a given antigen.

The antibodies described herein, e.g., recombinant, monoclonal, or polyclonal antibodies, may be prepared by any technique known in the art (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells. In embodiments, the antibodies described herein are humanized monoclonal antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. In embodiments, the antibodies described herein are chimeric monoclonal antibodies.

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa. In embodiments, the linker includes more than one serine. In embodiments, the linker includes more than one glycine. In embodiments, the linker includes at least one glycine and at least one serine.

The phrase "specifically (or selectively) binds" to an antibody or "specifically (or selectively) immunoreactive with," when referring to a protein refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (e.g., Harlow & Lane, Using Antibodies, A Laboratory Manual (1998) for a description of immunoassay formats and conditions that can be used to determine specific immunoreactivity).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

"Nucleic acid" refers to nucleotides (e.g., deoxyribonucleotides or ribonucleotides) and polymers thereof in either single-, double- or multiple-stranded form, or complements thereof; or nucleosides (e.g., deoxyribonucleosides or ribonucleosides). In embodiments, "nucleic acid" does not include nucleosides. The terms "polynucleotide," "oligonucleotide," "oligo" or the like refer, in the usual and customary sense, to a linear sequence of nucleotides. The term "nucleoside" refers, in the usual and customary sense, to a glycosylamine including a nucleobase and a five-carbon sugar (ribose or deoxyribose). Non limiting examples, of nucleosides include, cytidine, uridine, adenosine, guanosine, thymidine and inosine. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanosine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and a non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein the complementarity of sequences may be partial, in which only some of the nucleic acids match according to base pairing, or complete, where all the nucleic acids match according to base pairing. Thus, two sequences that are complementary to each other, may have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region).

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another: (1) alanine (A), glycine (G); (2) aspartic acid (D), glutamic acid (E); (3) asparagine (N), glutamine (Q); (4) arginine (R), lysine (K); (5) isoleucine (I), leucine (L), methionine (M), valine (V); (6) phenylalanine (F), tyrosine (Y), tryptophan (W); (7) serine (S), threonine (T); and (8) cysteine (C), methionine (M).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences or individual domains of the polypeptide sequence), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (e.g., Ausubel et al., Current Protocols in Molecular Biology (1995 supplement)).

An example of an algorithm that is suitable for determining percent sequence identity and sequence similarity are the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information (ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, less than about 0.01, or less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

An amino acid residue in an antibody "corresponds" to a given residue when it occupies the same essential structural position within the antibody as the given residue. For example, a selected residue in a comparison antibody corresponds to position 48 (according to the Kabat or Chothia numbering system) in an antibody provided herein when the selected residue occupies the same essential spatial or structural relationship to Kabat or Chothia position 48 as assessed using applicable methods in the art. For example, a comparison antibody may be aligned for maximum sequence homology with the antibody provided herein and the position in the aligned comparison antibody that aligns with Kabat or Chothia position 48 may be determined to correspond to it. Alternatively, instead of (or in addition to) a primary sequence alignment as described above, a three dimensional structural alignment can also be used, e.g., where the structure of the comparison antibody is aligned for maximum correspondence with an antibody provided herein and the overall structures compared. In this case, an amino acid that occupies the same essential position as Kabat or Chothia position 48 in the structural model may be said to correspond.

The term "isolated," when applied to a protein, denotes that the protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. The term "purified" denotes that a protein gives rise to essentially one band in an electrophoretic gel. Particularly, it means that the protein is at least 85% pure, at least 90% pure, at least 95% pure, or at least 99% pure.

The term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions. Additionally, some viral vectors are capable of targeting a particular cells type either specifically or non-specifically. Replication-incompetent viral vectors or replication-defective viral vectors refer to viral vectors that are capable of infecting their target cells and delivering their viral payload, but then fail to continue the typical lytic pathway that leads to cell lysis and death.

The term "chelating agent" is used according to its commonly known meaning in the art, and generally refers to organic or inorganic compounds capable of binding metal ions to form complex ring-like structure called chelates. In embodiments, a chelating agent has at least two functional groups which are able to form two or more coordinate covalent bonds with a metal ion.

Methods of Treatment

Provided herein are methods of treating cancer in a subject in need thereof comprising administering to the subject an effective amount of a radionuclide-labeled anti-CEA antibody, and an effective amount of an immunocytokine; wherein the immunocytokine is administered to the subject after the radionuclide-labeled anti-CEA antibody is administered to the subject. The radionuclide-labeled anti-CEA antibody is alternatively referred to as a first anti-CEA antibody bonded to a radionuclide, and is described in detail herein. The term "immunocytokine" refers to an anti-CEA antibody covalently bonded to a cytokine. The immunocytokine comprising an anti-CEA antibody covalently bonded to a cytokine is alternatively referred to as a second anti-CEA antibody bonded to a cytokine, and is described in detail herein.

Radionuclide-Labeled Antibodies

In embodiments, the disclosure provides a radionuclide-labeled anti-CEA antibody, also referred to as an anti-CEA antibody bonded to a radionuclide. In embodiments, the disclosure provides an anti-CEA antibody bonded to an alpha-emitting radionuclide. In embodiments, the disclosure provides a humanized anti-CEA antibody bonded to a radionuclide. In embodiments, the disclosure provides a humanized anti-CEA antibody bonded to an alpha-emitting radionuclide. In embodiments, the anti-CEA antibody bonded to the radionuclide is referred to herein as a "first anti-CEA antibody" in order to distinguish this anti-CEA antibody from the anti-CEA antibody bonded to the cytokine described herein. As such, the term "second anti-CEA antibody" refers to the anti-CEA antibody bonded to a cytokine.

The anti-CEA antibody can be any known in the art. In embodiments, the anti-CEA antibody is a humanized anti-CEA antibody. In embodiments, the anti-CEA antibody is M5A, M5B, T84.66, cibisatamab, MEDI-565 (also known as MTl 11 or AMG 211), labetuzamab, or NEO-201. In embodiments, the anti-CEA antibody is M5A, M5B, or T84.66. In embodiments, the anti-CEA antibody is M5A or M5B. In embodiments, the anti-CEA antibody is M5A. In embodiments, the anti-CEA antibody is M5B. In embodiments, the anti-CEA antibody is T84.66. In embodiments, the anti-CEA antibody is cibisatamab. In embodiments, the anti-CEA antibody is MEDI-565 (also known as MTl 11 or AMG 211). In embodiments, the anti-CEA antibody is labetuzamab. In embodiments, the anti-CEA antibody is NEO-201.

In embodiments, radionuclide is an alpha-emitting radionuclide. In embodiments, the alpha-emitting radionuclide is an isotope of actinium (Ac), an isotope of lead (Pb), an isotope of astatine (At), an isotope of thorium (Th), an isotope of bismuth (Bi), an isotope of radium (Ra), an isotope of terbium (Tb), or an isotope of uranium (U). In embodiments, the alpha-emitting radionuclide is an isotope of Ac. In embodiments, the alpha-emitting radionuclide is an isotope of Pb. In embodiments, the alpha-emitting radionuclide is an isotope of At. In embodiments, the alpha-emitting radionuclide is an isotope of Th. In embodiments, the alpha-emitting radionuclide is an isotope of Bi. In embodiments, the alpha-emitting radionuclide is an isotope of Ra. In embodiments, the alpha-emitting radionuclide is an isotope of Tb. In embodiments, the alpha-emitting radionuclide is an isotope of U. Alpha-emitting radionuclides are known in the art and described, for example, by Poty et al, J. Nucl Med. 59(6):878-884 (2018).

In embodiments, the alpha-emitting radionuclide is $^{225}$Ac, $^{212}$Pb, $^{210}$At, $^{21}$nAt, $^{226}$Th, $^{227}$Th, $^{212}$Bi, $^{213}$Bi, $^{223}$Ra, $^{224}$Ra, $^{149}$Tb, or $^{230}$U. In embodiments, the alpha-emitting radionuclide is $^{225}$Ac. In embodiments, the alpha-emitting radionuclide is $^{212}$Pb. In embodiments, the alpha-emitting radionuclide is $^{210}$At. In embodiments, the alpha-emitting radionuclide is $^{211}$At. In embodiments, the alpha-emitting radionuclide is $^{226}$Th. In embodiments, the alpha-emitting radionuclide is $^{227}$Th. In embodiments, the alpha-emitting radionuclide is $^{212}$Bi. In embodiments, the alpha-emitting radionuclide is $^{213}$Bi. In embodiments, the alpha-emitting radionuclide is $^{223}$Ra. In embodiments, the alpha-emitting radionuclide is $^{224}$Ra. In embodiments, the alpha-emitting radionuclide is $^{149}$Tb. In embodiments, the alpha-emitting radionuclide is $^{230}$U.

The term "bonded" with reference to an anti-CEA antibody "bonded" to a radionuclide alternatively refers to the anti-CEA antibody being "associated" with the radionuclide (e.g., alpha-emitting radionuclide) by any means known in the art. The association between the anti-CEA antibody and the radionuclide can be direct or indirect. In embodiments, the association between the anti-CEA antibody and the radionuclide is direct, e.g., whereby the radionuclide is directly bonded to the anti-CEA antibody. In embodiments, the term "bond" refers to covalent bonds, ionic bonds, hydrogen bonds, coordinate covalent bonds, and van der Waals interactions. In embodiments, the association between the anti-CEA antibody and radionuclide (e.g., alpha-emitting radionuclide) is indirect. An indirect association can occur when there is another molecule associated with the anti-CEA antibody and radionuclide (e.g., alpha-emitting radionuclide). For example, the anti-CEA antibody can be covalently bonded to a chelating agent, where the chelating agent is complexed with the radionuclide. In embodiments, the chelating agent/radionuclide complex can comprise coordinate covalent bonds between the chelating agent and the radionuclide. As another example, the anti-CEA antibody can be covalently bonded to a chemical moiety or a peptide, where the chemical moiety or peptide moiety is covalently bonded to the radionuclide. These embodiments are encompassed within the scope of an anti-CEA antibody bonded to a radionuclide (e.g., as an indirect association between the anti-CEA antibody and the radionuclide). A complex of a chelating agent and a radionuclide is known in the art and described, for example, by Akhaven et al, Cancer Biother Radiopharm, 35(1):10-15 (2020); and Liu et al, Materials, 3:3204-3217 (2010); doi:10.3390/ma3053204.

In embodiments, the chelating agent can be any chelating-agent known in the art that is capable of complexing or bonding with a radionuclide (e.g., an alpha-emitting radionuclide as described herein, including embodiments thereof). In embodiments, the chelating agent is DOTA, DOTA-2py, DOTA-3py, C-DOTA, PA-DOTA, DODASA, lys-DOTA, C-NOTA, NODASA, N-NOTA, TETA, 2C-TETA, 6C-TETA, BF-PEPA, BF-HEHA, DTPA, ca-DTPA, ibca-DTPA, 1B4M-DTPA, lys-DTPA, vinyl DTPA, glu-DTPA, EDTA, HEHA, macropa, py4pa, crown, bispa$^2$, CHXoctapa, Noneunpa, TCMC, Me-3,2-HOPA, macrocylic tetraphthalimide, CHX-A"-DTPA, $L^{Py}$, DOTP, 3p-C-NETA, or 3p-C-DEPA. In embodiments, the chelating agent is a C-NOTA, NODASA, or N-NOTA. In embodiments, the chelating agent is a TETA, 2C-TETA, 6C-TETA, BF-PEPA, or BF-HEHA. In embodiments, the chelating agent is DTPA, ca-DTPA, ibca-DTPA, 1B4M-DTPA, lys-DTPA, vinyl DTPA, or glu-DTPA. In embodiments, the chelating agent is DOTA, DOTA-2py, DOTA-3py, C-DOTA, PA-DOTA, DODASA, or lys-DOTA. In embodiments, the chelating agent is DOTA, HEHA, macropa, py4pa, crown, bispa$^2$, CHXoctapa, or Noneunpa. In embodiments, the chelating agent is DOTA. In embodiments, the chelating agent DOTA-2py. In embodiments, the chelating agent is DOTA-3py. In embodiments, the chelating agent is C-DOTA. In embodiments, the chelating agent is PA-DOTA. In embodiments, the chelating agent is DODASA. In embodiments, the chelating agent is lys-DOTA. In embodiments, the chelating agent is HEHA. In embodiments, the chelating agent is macropa. In embodiments, the chelating agent is py4pa. In embodiments, the chelating agent is crown. In embodiments, the chelating agent is bispa$^2$. In embodiments, the chelating agent is CHXoctapa. In embodiments, the chelating agent is a Noneunpa. The chemical structure of each of the chelating agents described herein is known in the art and described, for example, in Brechbiel, Q J Nucl Med Mol Imaging, 52(2):166-173 (2008); Yang et al, Journal of Nuclear Medicine, doi.org/10.2967/jnumed.121.262687; and Liu et al, Materials, 3:3204-3217 (2010). For example, it is known in the art that DOTA has the chemical name 1,4,7,10-tetraazacylcodecane-N,N',N",N"'-tetraacetic acid and the following chemical structure:

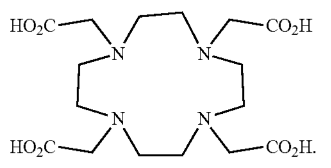 [SMILES: O=C(O)CN1CCN(CC(=O)O)CCN(CC(=O)O)CCN(CC(=O)O)CC1]

Methods for attaching chelating agents to antibodies are well-known in the art, e.g., Lewis et al, Bioconjugate Chem, 5(6):565-5765 (1994); Krejcarek et al, Biochemical and Biophysical Research Communications, 77(2):581-585 (1977); and Liu et al, Materials, 3:3204-3217 (2010). For example, Lewis et al, Bioconjugate Chem, 5(6):565-5765 (1994) provides a chemical synthetic scheme resulting in DOTA conjugated to an antibody, and having the following structure:

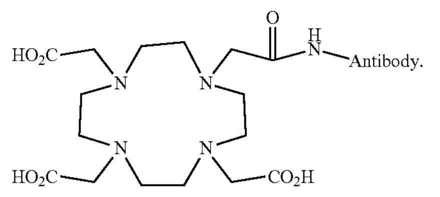

Chelating agents, such as DOTA, are complexed with radionuclides by methods known in the art, such as those described by Lewis et al, Bioconjugate Chem, 5(6):565-5765 (1994); Liu et al, Materials, 3:3204-3217 (2010); Poty et al, J. Nucl Med. 59(6):878-884 (2018); and Yang et al, Journal of Nuclear Medicine, doi.org/10.2967/jnumed.121.262687. In embodiments, the chelating agent is complexed with the radionuclide before the chelating agent is covalently bonded to the antibody. In embodiments, the chelating agent is complexed with the radionuclide after the chelating agent is covalently bonded to the antibody. In embodiments, the chelating agent is complexed with the radionuclide during the same reaction in which the chelating agent is covalently bonded to the antibody.

Immunocytokines

In embodiments, the disclosure provides an immunocytokine. In embodiments, the immunocytokine comprises an anti-CEA antibody bonded to a cytokine. In embodiments, the disclosure provides a humanized anti-CEA antibody bonded to a cytokine. The anti-CEA antibody can be any known in the art. In embodiments, the anti-CEA antibody is a humanized anti-CEA antibody. In embodiments, the anti-CEA antibody is M5A, M5B, T84.66, cibisatamab, MEDI-565 (also known as MT11 or AMG 211), labetuzamab, or NEO-201. In embodiments, the anti-CEA antibody is M5A, M5B, or T84.66. In embodiments, the anti-CEA antibody is M5A or M5B. In embodiments, the anti-CEA antibody is M5A. In embodiments, the anti-CEA antibody is M5B. In embodiments, the anti-CEA antibody is T84.66. In embodiments, the anti-CEA antibody is cibisatamab. In embodiments, the anti-CEA antibody is MEDI-565 (also known as MT111 or AMG 211). In embodiments, the anti-CEA antibody is labetuzamab. In embodiments, the anti-CEA antibody is NEO-201. As discussed above, the term "second anti-CEA antibody" refers to the anti-CEA antibody bonded to a cytokine in order to distinguish this anti-CEA antibody from the radionuclide-labeled anti-CEA antibody described herein. In embodiments, the first anti-CEA antibody and the second anti-CEA antibody are different antibodies (e.g., the first anti-CEA antibody is M5A and the second anti-CEA antibody is T84.66). In embodiments, the first anti-CEA antibody and the second anti-CEA antibody are the same antibody (e.g., the first anti-CEA antibody is M5A and the second anti-CEA antibody is M5A).

In embodiments, the immunocytokine comprises an anti-CEA antibody bonded to any cytokine known in the art. In embodiments, the cytokine is IL-2, IL-4, IL-7, IL-9, IL-12, IL-15, IL-21, IL-33, TNF-α, TGF-β, interferon-γ, or interferon-α. In embodiments, the cytokine is IL-2, IL-12, IL-15, IL-21, or interferon-α. In embodiments, the cytokine is IL-2, IL-12, or TNF-α. In embodiments, the cytokine is IL-2. In embodiments, the cytokine is IL-4. In embodiments, the cytokine is IL-7. In embodiments, the cytokine is IL-9. In embodiments, the cytokine is IL-12. In embodiments, the cytokine is IL-15. In embodiments, the cytokine is IL-21. In embodiments, the cytokine is IL-33. In embodiments, the cytokine is TNF-α. In embodiments, the cytokine is TGF-β. In embodiments, the cytokine is interferon-γ. In embodiments, the cytokine is interferon-α.

The immunocytokine can comprise the anti-CEA antibody bonded to the cytokine by any method known in the art. In embodiments, the anti-CEA antibody is covalently bonded to the cytokine. In embodiments, the anti-CEA antibody is covalently bonded to the cytokine via a peptide linking group. In embodiments, the anti-CEA antibody is covalently bonded to the cytokine by a chemical linking group. In embodiments, the immunocytokine is a fusion protein. In embodiments, the fusion protein comprises the anti-CEA antibody covalently bonded to the cytokine. In embodiments, the fusion protein comprises the anti-CEA antibody bonded to the cytokine via a peptide linking group. Methods of bonding an anti-CEA antibody to a cytokine are known in the art and described, for example, by Xu et al, Cancer Res, 60(16:4475-4484 (2000); and Kujawaki et al, Oncoimmunology, 9(1):e1724052 (2020).

Dosing Schedule

The first anti-CEA antibody bonded to the radionuclide is first administered to the subject, and after a period of time, the immunocytokine is administered to the subject, i.e., the immunocytokine is administered to the subject after the first anti-CEA antibody bonded to a radionuclide is administered to the subject. Thus, the first immunocytokine is not administered to the subject before the radionuclide-labeled antibody is administered to the subject. Similarly, the radionuclide-labeled anti-CEA antibody and the immunocytokine are not administered to the subject simultaneously.

The immunocytokine is administered to the subject after the first anti-CEA antibody bonded to a radionuclide is administered to the subject, where "after" is any period of time. In embodiments, the period of time between administration of the radionuclide-labeled antibody and administration of the immunocytokine is dependent upon the circulating half-life of the anti-CEA antibody and/or is dependent upon the half-life of the radionuclide in the radionuclide-labeled antibody. In embodiments, the immunocytokine is administered to the subject about the time of the half-life of the first anti-CEA antibody bonded to the radionuclide. In embodiments, the immunocytokine is administered to the subject about the time of the half-life of the radionuclide of the CEA antibody bonded to the radionuclide.

In embodiments, when the half-life of the circulating antibody (e.g., anti-CEA) in the blood is about 4 days, then the immunocytokine is administered to the subject about 3 days to about 6 days after the radionuclide-labeled antibody is administered to the subject. In embodiments, when the half-life of the circulating antibody in the blood is about 4 days, then the immunocytokine is administered to the subject 3 days after the radionuclide-labeled antibody is administered to the subject. In embodiments, when the half-life of the circulating antibody in the blood is about 4 days, then the immunocytokine is administered to the subject 4 days after the radionuclide-labeled antibody is administered to the subject. In embodiments, when the half-life of the circulating antibody in the blood is about 4 days, then the immunocytokine is administered to the subject 5 days after the radionuclide-labeled antibody is administered to the subject. In embodiments, when the half-life of the circulating antibody in the blood is about 4 days, then the immunocytokine is administered to the subject 6 days after the radionuclide-labeled antibody is administered to the subject.

In embodiments, when the half-life of the radionuclide (e.g., $^{225}$Ac) in the radionuclide-labeled antibody is about 10 days, then the immunocytokine is administered to the subject about 4 days to about 12 days after the radionuclide-labeled antibody is administered to the subject. In embodiments, when the half-life of the radionuclide in the radionuclide-labeled antibody is about 10 days, then the immunocytokine is administered to the subject about 5 days after the radionuclide-labeled antibody is administered to the subject. In embodiments, when the half-life of the radionuclide in the radionuclide-labeled antibody is about 10 days, then the immunocytokine is administered to the subject about 6 days after the radionuclide-labeled antibody is administered to the subject. In embodiments, when the half-life of the radionuclide in the radionuclide-labeled antibody is about 10 days, then the immunocytokine is administered to the subject about 7 days after the radionuclide-labeled antibody is administered to the subject. In embodiments, when the half-life of the radionuclide in the radionuclide-labeled antibody is about 10 days, then the immunocytokine is administered to the subject about 8 days after the radionuclide-labeled antibody is administered to the subject. In embodiments, when the half-life of the radionuclide in the radionuclide-labeled antibody is about 10 days, then the immunocytokine is administered to the subject about 9 days after the radionuclide-labeled antibody is administered to the subject. In embodiments, when the half-life of the radionuclide in the radionuclide-labeled antibody is about 10 days, then the immunocytokine is administered to the subject about 10 days after the radionuclide-labeled antibody is administered to the subject. In embodiments, when the half-life of the radionuclide in the radionuclide-labeled antibody is about 10 days, then the immunocytokine is administered to the subject about 11 days after the radionuclide-labeled antibody is administered to the subject. In embodiments, when the half-life of the radionuclide in the radionuclide-labeled antibody is about 10 days, then the immunocytokine is administered to the subject about 12 days after the radionuclide-labeled antibody is administered to the subject.

In embodiments, the immunocytokine is administered to the subject from about 1 hour to about 25 days after the first anti-CEA antibody is administered to the subject. In embodiments, the immunocytokine is administered to the subject from about 6 hours to about 25 days after the first anti-CEA antibody is administered to the subject. In embodiments, the immunocytokine is administered to the subject from about 12 hours to about 25 days after the first anti-CEA antibody is administered to the subject. In embodiments, the immunocytokine is administered to the subject about 1 day to about 25 days after the first anti-CEA antibody is administered to the subject. In embodiments, the immunocytokine is administered to the subject about 1 day to about 20 days after the first anti-CEA antibody is administered to the subject. In embodiments, the immunocytokine is administered to the subject about 1 day to about 15 days after the first anti-CEA antibody is administered to the subject. In embodiments, the immunocytokine is administered to the subject about 1 day to about 10 days after the first anti-CEA antibody is administered to the subject.

In embodiments, the immunocytokine is administered to the subject about 4 days to about 12 days after the first anti-CEA antibody is administered to the subject. In embodiments, the immunocytokine is administered to the subject about 5 days to about 12 days after the first anti-CEA antibody is administered to the subject. In embodiments, the immunocytokine is administered to the subject about 6 days to about 12 days after the first anti-CEA antibody is administered to the subject. In embodiments, the immunocytokine is administered to the subject about 7 days to about 12 days after the first anti-CEA antibody is administered to the subject. In embodiments, the immunocytokine is administered to the subject about 8 days to about 12 days after the first anti-CEA antibody is administered to the subject. In embodiments, the immunocytokine is administered to the subject about 9 days to about 12 days after the first anti-CEA antibody is administered to the subject. In embodiments, the immunocytokine is administered to the subject about 10 days to about 12 days after the first anti-CEA antibody is administered to the subject. In embodiments, the immunocytokine is administered to the subject about 11 days to about 12 days after the first anti-CEA antibody is administered to the subject.

In embodiments, the immunocytokine is administered to the subject about 4 days to about 11 days after the first anti-CEA antibody is administered to the subject. In embodiments, the immunocytokine is administered to the subject about 5 days to about 11 days after the first anti-CEA antibody is administered to the subject. In embodiments, the immunocytokine is administered to the subject about 6 days to about 11 days after the first anti-CEA antibody is administered to the subject. In embodiments, the immunocytokine is administered to the subject about 7 days to about 11 days after the first anti-CEA antibody is administered to the subject. In embodiments, the immunocytokine is administered to the subject about 8 days to about 11 days after the first anti-CEA antibody is administered to the subject. In embodiments, the immunocytokine is administered to the subject about 9 days to about 11 days after the first anti-CEA antibody is administered to the subject. In embodiments, the immunocytokine is administered to the subject about 10 days to about 11 days after the first anti-CEA antibody is administered to the subject.

In embodiments, the immunocytokine is administered to the subject about 4 days to about 10 days after the first anti-CEA antibody is administered to the subject. In embodiments, the immunocytokine is administered to the subject about 5 days to about 10 days after the first anti-CEA antibody is administered to the subject. In embodiments, the immunocytokine is administered to the subject about 6 days to about 10 days after the first anti-CEA antibody is administered to the subject. In embodiments, the immunocytokine is administered to the subject about 7 days to about 10 days after the first anti-CEA antibody is administered to the subject. In embodiments, the immunocytokine is administered to the subject about 8 days to about 10 days after the first anti-CEA antibody is administered to the subject. In embodiments, the immunocytokine is administered to the subject about 9 days to about 10 days after the first anti-CEA antibody is administered to the subject.

In embodiments, the immunocytokine is administered to the subject about 1 day after the first anti-CEA antibody is administered to the subject. In embodiments, the immunocytokine is administered to the subject about 2 days after the first anti-CEA antibody is administered to the subject. In embodiments, the immunocytokine is administered to the subject about 3 days after the first anti-CEA antibody is administered to the subject. In embodiments, the immunocytokine is administered to the subject about 4 days after the first anti-CEA antibody is administered to the subject. In embodiments, the immunocytokine is administered to the subject about 5 days after the first anti-CEA antibody is administered to the subject. In embodiments, the immunocytokine is administered to the subject about 6 days after the first anti-CEA antibody is administered to the subject. In embodiments, the immunocytokine is administered to the subject about 7 days after the first anti-CEA antibody is administered to the subject. In embodiments, the immunocytokine is administered to the subject about 8 days after the first anti-CEA antibody is administered to the subject. In embodiments, the immunocytokine is administered to the subject about 9 days after the first anti-CEA antibody is administered to the subject. In embodiments, the immunocytokine is administered to the subject about 10 days after the first anti-CEA antibody is administered to the subject. In embodiments, the immunocytokine is administered to the subject about 11 days after the first anti-CEA antibody is administered to the subject. In embodiments, the immunocytokine is administered to the subject about 12 days after the first anti-CEA antibody is administered to the subject. In embodiments, the immunocytokine is administered to the subject about 13 days after the first anti-CEA antibody is administered to the subject. In embodiments, the immunocytokine is administered to the subject about 14 days after the first anti-CEA antibody is administered to the subject. In embodiments, the immunocytokine is administered to the subject about 15 days after the first anti-CEA antibody is administered to the subject. In embodiments, the immunocytokine is administered to the subject about 16 days after the first anti-CEA antibody is administered to the subject. In embodiments, the immunocytokine is administered to the subject about 17 days after the first anti-CEA antibody is administered to the subject. In embodiments, the immunocytokine is administered to the subject about 18 days after the first anti-CEA antibody is administered to the subject. In embodiments, the immunocytokine is administered to the subject about 19 days after the first anti-CEA antibody is administered to the subject. In embodiments, the immunocytokine is administered to the subject about 20 days after the first anti-CEA antibody is administered to the subject. In embodiments, the immunocytokine is administered to the subject about 21 days after the first anti-CEA antibody is administered to the subject. In embodiments, the immunocytokine is administered to the subject about 22 days after the first anti-CEA antibody is administered to the subject. In embodiments, the immunocytokine is administered to the subject about 23 days after the first anti-CEA antibody is administered to the subject. In embodiments, the immunocytokine is administered to the subject about 24 days after the first anti-CEA antibody is administered to the subject. In embodiments, the immunocytokine is administered to the subject about 25 days after the first anti-CEA antibody is administered to the subject.

The skilled artisan will appreciate that this dosing order (i.e., radionuclide-labeled antibody administered first, and immunocytokine administered second) refers to the first treatment cycle of the radionuclide-labeled antibody and immunocytokine therapy. After the first treatment cycle, the subject can be administered a second treatment cycle (and third treatment cycle, etc) whereby the immunocytokine is administered to the subject after the radionuclide-labeled anti-CEA antibody is administered to the subject in each treatment cycle. The skilled artisan will readily appreciate that the second treatment cycle will necessarily follow the first treatment cycle, and that in each treatment cycle the radionuclide-labeled anti-CEA antibody is administered to the subject before the immunocytokine is administered to the subject. In embodiments, the second (or third, or fourth) treatment cycle begins at least one week after the immunocytokine is administered to the subject in the first (or second, or third, respectively) treatment cycle. In embodiments, the second (or third, or fourth) treatment cycle begins at least two weeks after the immunocytokine is administered to the subject in the first (or second, or third, respectively) treatment cycle. In embodiments, the second (or third, or fourth) treatment cycle begins at least three weeks after the immunocytokine is administered to the subject in the first (or second, or third, respectively) treatment cycle. In embodiments, the second (or third, or fourth) treatment cycle begins at least four weeks after the immunocytokine is administered to the subject in the first (or second, or third, respectively) treatment cycle. In embodiments, the second (or third, or fourth) treatment cycle begins about one week to about 1 month after the immunocytokine is administered to the subject in the first (or second, or third, respectively) treatment cycle. In embodiments, the second (or third, or fourth) treatment cycle begins about two weeks to about four weeks after the immunocytokine is administered to the subject in the first (or second, or third, respectively) treatment cycle. In embodiments, the second (or third, or fourth) treatment cycle begins about two weeks to about three weeks after the immunocytokine is administered to the subject in the first (or second, or third, respectively) treatment cycle.

In embodiments, the immunocytokine is administered one to four times per day. In embodiments, the immunocytokine is administered one to three times per day. In embodiments, the immunocytokine is administered one to two times per day. In embodiments, the immunocytokine is administered once per day. In embodiments, the immunocytokine is administered twice per day. In embodiments, the immunocytokine is administered three times per day. In embodiments, the immunocytokine is administered four times per day.

In embodiments, the immunocytokine is administered to the subject daily for 1 day to about 6 months. In embodiments, the immunocytokine is administered to the subject daily for about 1 week to about 6 months. In embodiments, the immunocytokine is administered to the subject daily for about 1 week to about 5 months. In embodiments, the immunocytokine is administered to the subject daily for about 1 week to about 4 months. In embodiments, the immunocytokine is administered to the subject daily for about 1 week to about 3 months. In embodiments, the immunocytokine is administered to the subject daily for about 1 week to about 2 months. In embodiments, the immunocytokine is administered to the subject daily for about 1 week to about 1 month. In embodiments, the immunocytokine is administered to the subject daily for about 1 week to about 6 weeks. In embodiments, the immunocytokine is administered to the subject daily for about 2 weeks to about 6 weeks. In embodiments, the immunocytokine is administered to the subject daily for about 2 weeks to about 4 weeks. In embodiments, the immunocytokine is administered to the subject daily for about 2 weeks to about 3 weeks.

In embodiments, the methods comprise treating cancer. The term "cancer" refers to all types of cancer, neoplasm or malignant tumors found in mammals (e.g., humans), including leukemia, lymphoma, carcinomas and sarcomas. Exemplary cancers that may be treated with a compound or method provided herein include thyroid cancer, endocrine system cancer, brain cancer, breast cancer, cervical cancer, ovarian cancer, colon cancer, colorectal cancer, rectal cancer, head and neck cancer, liver cancer, kidney cancer, lung cancer (e.g., non-small cell lung cancer, small cell lung cancer), melanoma, mesothelioma, stomach cancer, uterine cancer medulloblastoma, multiple myeloma, and pancreatic cancer. Additional examples of cancer include Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, thyroid cancer, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

In embodiments, the methods comprise treating any cancer that is responsive to treatment with an anti-CEA antibody. In embodiments, the methods comprise treating a cancer that expresses a carcinoembryonic antigen. In embodiments, the methods comprise treating a cancer that overexpresses a carcinoembryonic antigen. In embodiments, the methods comprise treating a cancer that overexpresses a carcinoembryonic antigen relative to a control. In embodiments, the cancer is colon cancer, colorectal cancer, rectal cancer, breast cancer, pancreatic cancer, lung cancer, ovarian cancer, multiple myeloma, stomach cancer, thyroid cancer, or head and neck cancer. In embodiments, the cancer is colon cancer or breast cancer. In embodiments, the cancer is colon cancer. In embodiments, the cancer is breast cancer. In embodiments, the cancer is colorectal cancer. In embodiments, the cancer is rectal cancer. In embodiments, the cancer is pancreatic cancer. In embodiments, the cancer is lung cancer. In embodiments, the cancer is small cell lung cancer. In embodiments, the cancer is non-small cell lung cancer. In embodiments, the cancer is ovarian cancer. In embodiments, the cancer is multiple myeloma. In embodiments, the cancer is stomach cancer. In embodiments, the cancer is thyroid cancer. In embodiments, the cancer is head and neck cancer.

A "control" refers to a sample that serves as a reference, usually a known reference, for comparison to a test sample. For example, a test sample can be taken from a patient having cancer and compared to samples from a known cancer patient or a known normal (non-disease) individual. A control can also represent an average value gathered from a population of similar individuals, e.g., cancer patients or healthy individuals with a similar medical background, same age, weight, etc. A control value can also be obtained from the same individual, e.g., from an earlier-obtained sample, prior to disease, or prior to treatment. One of skill will recognize that controls can be designed for assessment of any number of parameters. In embodiments, a control is a negative control. In embodiments, a control comprises the average amount of expression (e.g., protein or nucleic acid) of infiltration (e.g., number or percentage of cells in a population of cells) in a population of subjects with cancer or in a healthy or general population. In embodiments, the control comprises an average amount (e.g. percentage or number of infiltrating cells or amount of expression) in a population in which the number of subjects (n) is 5 or more, 10 or more, 25 of more, 50 or more, 100 or more, 1000 or more, 5000 or more, or 10000 or more. In embodiments, the control is a standard control. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

In embodiments, the methods described herein further comprise administering to the subject an anti-cancer agent, radiation therapy, or a combination thereof. In embodiments, the methods further comprise administering to the subject an anti-cancer agent. In embodiments, the methods further comprising administering to the subject radiation therapy. In embodiments, the methods further comprise administering to the subject an anti-cancer agent and radiation therapy. In embodiments, the anti-cancer agent is a radiosensitizer.

In embodiments, the methods described herein further comprise administering to the subject an effective amount of a radiosensitizer. In embodiments, the radiosensitizer is a hypoxic cell sensitizer, a hypoxic cytotoxin, or a nonhypoxic cell sensitizer. In embodiments, the radiosensitizer is a hypoxic cell sensitizer. In embodiments, the radiosensitizer is a hypoxic cytotoxin. In embodiments, the radiosensitizer is a nonhypoxic cell sensitizer. In embodiments, the radiosensitizer is NBTXR3, nitroimidazole, paclitaxel, docetaxel, irinotecan, nicotinamide, misonidazole, etanidazole, nimorazole, mitomycin-C, tirapazamine, procaine, lidocaine, chlorpromazine, 5-fluorouracil, floxuridine, bromodeoxyuridine, idoxuridine, hydroxyurea, gemcitabine, fludarabine, efaproxiral, trans sodium crocetinate, NVX-108, or a combination of two or more thereof.

"Anti-cancer agent" and "anticancer agent" are used in accordance with their plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rlL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta *Medica*), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, Inanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), immunotherapy (e.g., cellular immunotherapy, antibody therapy, cytokine therapy, combination immunotherapy, etc.), radioimmunotherapy (e.g., anti-CD20 monoclonal antibody conjugated to $^{111}In$, $^{90}Y$, or $^{131}I$, etc.), immune checkpoint inhibitors (e.g., CTLA4 blockade, PD-1 inhibitors, PD-L1 inhibitors, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

Compositions

Provided herein are compositions comprising the anti-CEA antibodies described herein (including embodiments and aspects thereof) and a pharmaceutically acceptable excipient.

"Pharmaceutically acceptable excipient" refers to a substance that aids the administration of an active agent to and absorption by a subject and can be included in the compositions of the disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such compositions can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the antibodies of the disclosure. One of skill in the art will recognize that other pharmaceutical excipients are useful. The term "excipient" can be used interchangeably with other terms of art, such as "carrier" or "diluent."

Solutions of the antibodies can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these compositions can contain a preservative to prevent the growth of microorganisms.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the antibodies in the required amount in the appropriate solvent followed by filtered sterilization. Generally, dispersions are prepared by incorporating the antibodies into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The composition of more, or highly, concentrated solutions for direct injection is also contemplated. Solvents, such as dimethyl sulfoxide, can be used for extremely rapid penetration, delivering high concentrations of the active agents to a small area.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic compositions and appropriate drug stabilizers, if required, may be included in the formulation. Various commercial nasal compositions are known.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In aspects, oral pharmaceutical compositions will comprise an inert diluent or edible carrier, or they may be enclosed in hard or soft shell gelatin capsule, or they may be compressed into tablets, or they may be incorporated directly with the food. For oral therapeutic administration, the antibodies may be incorporated with excipients and used in the form of ingestible tablets, buccal tablets, troches, capsules, elixirs, suspensions, syrups, wafers, and the like. The percentage of the compositions may, of course, be varied and may conveniently be between about 1 to about 75% of the weight of the unit. The amount of antibodies in such compositions is such that a suitable dosage can be obtained.

The formulations of antibodies can be presented in unit-dose or multi-dose sealed containers, such as ampules and vials. Thus, the composition can be in unit dosage form. In such form the composition is subdivided into unit doses containing appropriate quantities of antibodies. Thus, the compositions can be administered in a variety of unit dosage forms depending upon the method of administration.

The term "administering" means oral administration, administration as a suppository, topical contact, intravenous, parenteral, intraperitoneal, intramuscular, intralesional, intrathecal, intranasal, or subcutaneous administration to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent. In embodiments, administering refers to intravenous administration or subcutaneous administration. In embodiments, administering refers to intravenous administration. In embodiments, administering refers to subcutaneous administration.

The terms "treating" or "treatment" refers to any indicia of success in the therapy or amelioration of a disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

The term "prevent" refers to a decrease in the occurrence of disease symptoms in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease or condition that can be treated by administration of a pharmaceutical composition as provided herein. Non-limiting examples include humans, other mammals, bovines, dogs, monkeys, and other non-mammalian animals. In some embodiments, a patient is human.

Dosages

Pharmaceutical compositions include compositions wherein the active ingredient (i.e., anti-CEA antibodies) is contained in a therapeutically effective amount, i.e., in an amount effective to achieve its intended purpose. The actual amount effective for a particular application will depend, inter alia, on the condition being treated, as judged by a practitioner in the medical arts.

A "effective amount" is an amount sufficient for an antibody to accomplish a stated purpose relative to the absence of the compound (e.g. achieve the effect for which it is administered, treat a disease, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of an antibody is an amount of that antibody, when administered to a subject, will have the intended prophylactic effect, e.g., preventing or delaying the onset (or reoccurrence) of a disease, pathology or condition, or reducing the likelihood of the onset (or reoccurrence) of a disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

For any antibody described herein, the therapeutically effective amount can be initially determined from cell culture assays. Target concentrations will be those concentrations of antibody that are capable of achieving the methods described herein, as measured using the methods described herein or known in the art. As is well known in the art, therapeutically effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages and frequency (single or multiple doses) of the antibodies may be varied depending upon the requirements of the patient. The dose administered to a patient should be sufficient to affect a beneficial therapeutic response in the patient over time. The size of the dose also will be determined by the existence, nature, and extent of any adverse side-effects. Determination of the proper dosage for a particular situation is within the skill of the art. Generally, treatment is initiated with smaller dosages which are less than the optimum dose of the antibody. Thereafter, the dosage is increased by small increments until the optimum effect under circumstances is reached. Dosage amounts and intervals can be adjusted individually to provide levels of the antibody effective for the particular clinical indication being treated. This will provide a therapeutic regimen that is commensurate with the severity of the individual's disease state. In embodiments, the antibody is administered at an amount from about 0.001 μg to about 10,000 μg.

In embodiments, the radionuclide-labeled anti-CEA antibody (i.e., first anti-CEA antibody bonded to the alpha-emitting radionuclide) is administered to the subject in an amount from about 1 $mCi/m^2$ to about 50 $mCi/m^2$. In embodiments, the radionuclide-labeled anti-CEA antibody is administered to the subject in an amount from about 1 $mCi/m^2$ to about 40 $mCi/m^2$. In embodiments, the radionuclide-labeled anti-CEA antibody is administered to the subject in an amount from about 1 $mCi/m^2$ to about 35 $mCi/m^2$. In embodiments, the radionuclide-labeled anti-CEA antibody is administered to the subject in an amount from about 1 $mCi/m^2$ to about 30 $mCi/m^2$. In embodiments, the radionuclide-labeled anti-CEA antibody is administered to the subject in an amount from about 1 $mCi/m^2$ to about 25 $mCi/m^2$. In embodiments, the radionuclide-labeled anti-CEA antibody is administered to the subject in an amount from about 5 $mCi/m^2$ to about 50 $mCi/m^2$. In embodiments, the radionuclide-labeled anti-CEA antibody is administered to the subject in an amount from about 5 $mCi/m^2$ to about 30 $mCi/m^2$. In embodiments, the radionuclide-labeled anti-CEA antibody is administered to the subject in an amount from about 5 $mCi/m^2$ to about 25 $mCi/m^2$. In embodiments, the radionuclide-labeled anti-CEA antibody is administered to the subject in an amount from about 5 $mCi/m^2$ to about 20 $mCi/m^2$.

In embodiments, the immunocytokine (i.e., second anti-CEA antibody bonded to the cytokine) is administered to the subject in an amount from about 0.1 mg per dose to about 25 mg per dose. In embodiments, the immunocytokine is administered to the subject in an amount from about 1 mg per dose to about 25 mg per dose. In embodiments, the immunocytokine is administered to the subject in an amount from about 0.1 mg per dose to about 20 mg per dose. In embodiments, the immunocytokine is administered to the subject in an amount from about 1 mg per dose to about 20 mg per dose. In embodiments, the immunocytokine is administered to the subject in an amount from about 0.7 mg per dose to about 7.0 mg per dose. In embodiments, the immunocytokine is administered to the subject in an amount from about 0.01 mg/kg per dose to about 0.10 mg/kg per dose.

In embodiments, the immunocytokine (i.e., second anti-CEA antibody bonded to the cytokine) is administered to the subject in an amount from about 1 Mio IU cytokine equivalent per dose to about 50 Mio IU cytokine equivalent per dose. In embodiments, the immunocytokine is administered to the subject in an amount from about 1 Mio IU cytokine equivalent per dose to about 30 Mio IU cytokine equivalent per dose. In embodiments, the immunocytokine is administered to the subject in an amount from about 1 Mio IU cytokine equivalent per dose to about 25 Mio IU cytokine equivalent per dose. In embodiments, the immunocytokine is administered to the subject in an amount from about 5 Mio IU cytokine equivalent per dose to about 50 Mio IU cytokine equivalent per dose. In embodiments, the immunocytokine is administered to the subject in an amount from about 5 Mio IU cytokine equivalent per dose to about 30 Mio IU cytokine equivalent per dose. In embodiments, the immunocytokine is administered to the subject in an amount from about 5 Mio IU cytokine equivalent per dose to about 25 Mio IU cytokine equivalent per dose. The skilled artisan will appreciate that "Mio IU" or "MIU" refers to million international units.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of monoclonal antibodies by considering factors such as compound potency, relative bioavailability, patient body weight, presence and severity of adverse side effects.

Kits

Provided herein are kits comprising the first anti-carcinoembryonic antigen (CEA) antibody bonded to an alpha-emitting radionuclide; and an immunocytokine comprising a second anti-CEA antibody covalently bonded to a cytokine. In embodiments, the kits further comprise instructions for us. The kits can optionally comprise syringes, needles, sterile water vials for injection, and the like.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Embodiments 1 to 48

Embodiment 1. A humanized anti-carcinoembryonic antigen (CEA) antibody, wherein the humanized anti-CEA antibody is bonded to an alpha-emitting radionuclide.

Embodiment 2. The humanized anti-CEA antibody of Embodiment 1, wherein the humanized anti-CEA antibody has a variable light chain domain of SEQ ID NO:8 and a variable heavy chain domain of SEQ ID NO:9.

Embodiment 3. The humanized anti-CEA antibody of Embodiment 1, wherein the humanized anti-CEA antibody has a variable light chain domain of SEQ ID NO:8 and a variable heavy chain domain of SEQ ID NO:10.

Embodiment 4. The humanized anti-CEA antibody of Embodiment 1, wherein the humanized anti-CEA antibody has a CDR-L1 as in SEQ ID NO:1, a CDR-L2 as in SEQ ID NO:2, a CDR-L3 as in SEQ ID NO:3, a CDR-H1 as in SEQ ID NO:4, a CDR-H2 as in SEQ ID NO:5 or SEQ ID NO:7, and a CDR-H3 as in SEQ ID NO:6.

Embodiment 5. The humanized anti-CEA antibody of any one of Embodiments 1 to 4, wherein the alpha-emitting radionuclide is an isotope of actinium, an isotope of lead, an isotope of astatine, an isotope of thorium, an isotope of bismuth, an isotope of radium, an isotope of terbium, or an isotope of uranium.

Embodiment 6. The humanized anti-CEA antibody of any one of Embodiments 1 to 4, wherein the alpha-emitting radionuclide is s $^{225}$Ac, $^{212}$Pb, $^{210}$At, $^{211}$At, $^{226}$Th, $^{227}$Th, $^{212}$Bi, $^{213}$Bi, $^{223}$Ra, $^{224}$Ra, $^{149}$Tb, or $^{213}$U.

Embodiment 7. The humanized anti-CEA antibody of any one of Embodiments 1 to 4, wherein the alpha-emitting radionuclide is $^{225}$Ac.

Embodiment 8. The humanized anti-CEA antibody of any one of Embodiments 1 to 7, wherein the alpha-emitting radionuclide is complexed with a chelating agent moiety; and wherein the chelating agent moiety is covalently bonded to the humanized anti-CEA antibody.

Embodiment 9. The humanized anti-CEA antibody of Embodiment 8, wherein the chelating agent is DOTA, DOTA-2py, DOTA-3py, C-DOTA, PA-DOTA, DODASA, lys-DOTA, C-NOTA, NODASA, N-NOTA, TETA, 2C-TETA, 6C-TETA, BF-PEPA, BF-HEHA, DTPA, ca-DTPA, ibca-DTPA, 1B4M-DTPA, lys-DTPA, vinyl DTPA, glu-DTPA, EDTA, HEHA, macropa, py4pa, crown, bispa$^2$, CHXoctapa, Noneunpa, TCMC, Me-3,2-HOPA, macrocylic tetraphthalimide, CHX-A"-DTPA, $L^{Py}$, DOTP, 3p-C-NETA, or 3p-C-DEPA.

Embodiment 10. The humanized anti-CEA antibody of Embodiment 8, wherein the chelating agent is DOTA, HEHA, macropa, py4pa, crown, bispa$^2$, CHXoctapa, or Noneunpa.

Embodiment 11. The humanized anti-CEA antibody of Embodiment 8, wherein the chelating agent is DOTA.

Embodiment 12. The humanized anti-CEA antibody of Embodiment 1, wherein the humanized anti-CEA antibody has a variable light chain domain of SEQ ID NO:8 and a variable heavy chain domain of SEQ ID NO:9; wherein the alpha-emitting radionuclide is $^{225}$Ac; wherein the alpha-emitting radionuclide is complexed with a chelating agent; wherein the chelating agent is DOTA; and wherein the chelating agent is covalently bonded to the humanized anti-CEA antibody.

Embodiment 13. A method of treating cancer in a subject in need thereof, the method comprising administering to the subject an effective amount of: (i) a first anti-carcinoembryonic antigen (CEA) antibody bonded to an alpha-emitting radionuclide, and (ii) an immunocytokine comprising a second anti-carcinoembryonic antigen (CEA) antibody covalently bonded to a cytokine; wherein the immunocytokine is administered to the subject after the first anti-CEA antibody bonded to the alpha-emitting radionuclide is administered to the subject.

Embodiment 14. The method of Embodiment 13, wherein the first anti-CEA antibody is a humanized anti-CEA antibody.

Embodiment 15. The method of Embodiment 13 or 14, wherein the second anti-CEA antibody is a humanized anti-CEA antibody.

Embodiment 16. The method of any one of Embodiments 13 to 15, wherein the first anti-CEA antibody and the second anti-CEA antibody have a CDR-L1 as in SEQ ID NO:1, a CDR-L2 as in SEQ ID NO:2, a CDR-L3 as in SEQ ID NO:3, a CDR-H1 as in SEQ ID NO:4, a CDR-H2 as in SEQ ID NO:5 or SEQ ID NO:7, and a CDR-H3 as in SEQ ID NO:6.

Embodiment 17. The method of Embodiment 13, wherein the first anti-CEA antibody and the second anti-CEA antibody have a variable light chain domain of SEQ ID NO:8 and a variable heavy chain domain of SEQ ID NO:9.

Embodiment 18. The method of Embodiment 13, wherein the first anti-CEA antibody and the second anti-CEA antibody have a variable light chain domain of SEQ ID NO:8 and a variable heavy chain domain of SEQ ID NO:10.

Embodiment 19. The method of Embodiment 13, wherein the first anti-CEA antibody and the second anti-CEA antibody have a variable light chain domain of SEQ ID NO:11 and a variable heavy chain domain of SEQ ID NO:12.

Embodiment 20. The method of any one of Embodiments 13 to 19, wherein the alpha-emitting radionuclide is an isotope of actinium, an isotope of lead, an isotope of astatine, an isotope of thorium, an isotope of bismuth, an isotope of radium, an isotope of terbium, or an isotope of uranium.

Embodiment 21. The method of any one of Embodiments 13 to 19, wherein the alpha-emitting radionuclide is $^{225}$Ac, $^{212}$Pb, $^{210}$At, $^{211}$At, $^{226}$Th, $^{227}$Th, $^{212}$Bi, $^{213}$Bi, $^{223}$Ra, $^{224}$Ra, $^{149}$Tb, or $^{230}$U.

Embodiment 22. The method of any one of Embodiments 13 to 19, wherein the alpha-emitting radionuclide is $^{225}$Ac.

Embodiment 23. The method of any one of Embodiments 13 to 22, wherein the alpha-emitting radionuclide is complexed with a chelating agent; and wherein the chelating agent is covalently bonded to the first anti-CEA antibody.

Embodiment 24. The method of Embodiment 23, wherein the chelating agent is DOTA, DOTA-2py, DOTA-3py, C-DOTA, PA-DOTA, DODASA, lys-DOTA, C-NOTA, NODASA, N-NOTA, TETA, 2C-TETA, 6C-TETA, BF-PEPA, BF-HEHA, DTPA, ca-DTPA, ibca-DTPA, 1B4M-DTPA, lys-DTPA, vinyl DTPA, glu-DTPA, EDTA, HEHA, macropa, py4pa, crown, bispa$^2$, CHXoctapa, Noneunpa, TCMC, Me-3,2-HOPA, macrocylic tetraphthalimide, CHX-A"-DTPA, $L^{Py}$, DOTP, 3p-C-NETA, or 3p-C-DEPA.

Embodiment 25. The method of Embodiment 23, wherein the chelating agent is DOTA, HEHA, macropa, py4pa, crown, bispa$^2$, CHXoctapa, or Noneunpa.

Embodiment 26. The method of Embodiment 23, wherein the chelating agent is DOTA.

Embodiment 27. The method of any one of Embodiments 13 to 26, wherein the cytokine is IL-2, IL-4, IL-7, IL-9, IL-12, IL-15, IL-21, IL-33, TNF-α, TGF-β, interferon-γ, or interferon-α.

Embodiment 28. The method of any one of Embodiments 13 to 26, wherein the cytokine is IL-2.

Embodiment 29. The method of any one of Embodiments 13 to 28, wherein the immunocytokine is administered to the subject about 1 day to about 25 days after the first anti-CEA antibody is administered to the subject.

Embodiment 30. The method of any one of Embodiments 13 to 28, wherein the immunocytokine is administered to the subject about 5 days to about 10 days after the first anti-CEA antibody is administered to the subject.

Embodiment 31. A method of treating cancer in a subject in need thereof, the method comprising administering to the subject an effective amount of: (i) the humanized anti-carcinoembryonic antigen (CEA) antibody of claim 12, and (ii) a fusion protein comprising a second humanized anti-CEA antibody covalently bonded to a cytokine; wherein the humanized anti-CEA antibody has a variable light chain domain of SEQ ID NO:8 and a variable heavy chain domain of SEQ ID NO:9; and wherein the cytokine is IL-2; wherein the fusion protein is administered to the subject about 5 days to about 10 days after the humanized anti-CEA antibody is administered to the subject.

Embodiment 32. The method of any one of Embodiments 13 to 31, wherein the effective amount of the first anti-CEA antibody bonded to the alpha-emitting radionuclide is from about 1 mCi/m$^2$ to about 50 mCi/m$^2$.

Embodiment 33. The method of any one of Embodiments 13 to 31, wherein the effective amount of the first anti-CEA antibody bonded to the alpha-emitting radionuclide is from about 5 mCi/m$^2$ to about 20 mCi/m$^2$.

Embodiment 34. The method of any one of Embodiments 13 to 33, wherein the effective amount of the immunocytokine is from about 0.17 mg per dose to about 7 mg per dose.

Embodiment 35. The method of any one of Embodiments 13 to 33, wherein the effective amount of the immunocytokine is from about 1 Mio IU cytokine equivalent per dose to about 50 Mio IU cytokine equivalent per dose.

Embodiment 36. The method of any one of Embodiments 13 to 33, wherein the effective amount of the immunocytokine is from about 5 Mio IU cytokine equivalent per dose to about 30 Mio IU cytokine equivalent per dose.

Embodiment 37. The method of any one of Embodiments 13 to 36, wherein the immunocytokine is administered to the subject 1 time per day to 4 times per day.

Embodiment 38. The method of any one of Embodiments 13 to 37, wherein the immunocytokine is administered to the subject daily for 1 day to about 6 months.

Embodiment 39. The method of any one of Embodiments 13 to 37, wherein the immunocytokine is administered to the subject daily for 1 week to about 2 months.

Embodiment 40. The method of any one of Embodiments 13 to 37, wherein the immunocytokine is administered to the subject daily for about 2 weeks to about 6 weeks.

Embodiment 41. The method of any one of Embodiments 13 to 40, wherein the first anti-CEA antibody bonded to the alpha-emitting radionuclide is administered to the subject intravenously or subcutaneously.

Embodiment 42. The method of any one of Embodiments 13 to 41, wherein the immunocytokine is administered to the subject intravenously or subcutaneously.

Embodiment 43. The method of any one of Embodiments 13 to 42, further comprising administering to the subject an effective amount of a radiosensitizer.

Embodiment 44. The method of Embodiment 43, wherein the radiosensitizer is nitroimidazole, paclitaxel, docetaxel, irinotecan, nicotinamide, misonidazole, etanidazole, nimorazole, mitomycin-C, tirapazamine, procaine, lidocaine, chlorpromazine, 5-fluorouracil, floxuridine, bromodeoxyuridine, idoxuridine, hydroxyurea, gemcitabine, fludarabine, or efaproxiral.

Embodiment 45. The method of any one of Embodiments 13 to 44, wherein the cancer overexpresses a carcinoembryonic antigen relative to a control.

Embodiment 46. The method of any one of Embodiments 13 to 45, wherein the cancer is colon cancer, colorectal cancer, rectal cancer, breast cancer, pancreatic cancer, lung cancer, ovarian cancer, multiple myeloma, stomach cancer, thyroid cancer, or head and neck cancer.

Embodiment 47. The method of Embodiment 46, wherein the cancer is colon cancer or breast cancer.

Embodiment 48. A kit for treating cancer, the kit comprising: (i) a first anti-carcinoembryonic antigen (CEA) antibody bonded to an alpha-emitting radionuclide; (ii) an immunocytokine comprising a second anti-CEA antibody covalently bonded to a cytokine; and (iii) instructions for use.

EXAMPLES

Targeted alpha therapy (TAT) delivers high linear transfer energy alpha particles to tumors with the potential to generate an immune response at the tumor site that may be augmented by immunotherapy. In order to evaluate this concept, the animal model must have an intact immune system that expresses the tumor antigen of interest. Thus, we have treated CEA transgenic mice that bear CEA positive murine mammary or colon tumors with a combination of $^{225}$sAc-DOTA labeled anti-CEA humanized antibody M5A and the immunocytokine M5A-IL2. $^{225}$Ac was chosen for its long half-life (10 day) and emission of 4 alpha particles. In a dose response (3.7, 7.4 and 11.1 kBq) study of TAT only for orthotopic CEA positive mammary tumors, the highest dose gave a delay in tumor growth of 30 days and an increase in median survival from 20 days to 36 days. ICK (4× daily) only gave a tumor growth delay of 20 days that was not improved by combination with 7.4 kBq of TAT post ICK treatment. However, TAT (7.4 kBq) followed by ICK 10 days later (4× daily) led to a delay in tumor growth of 38 days with an increase of median survival to 45 days. Similar results were seen for ICK at 5 days to 10 days after TAT. When a similar study was performed with subcutaneous implanted CEA positive MC38 colon tumors, TAT (11.1 kBq) only gave an increase in median survival from 30 days to 50 days, and with the addition of ICK 5 days post TAT of 57 days. Increased tumor infiltrating IFNg$^+$CD8$^+$ T-cells and an increased ratio of these cells to CD4$^+$ Tegs with combined therapy indicates that ICK augmented TAT leads to an immune response that improves tumor therapy.

The combination of RIT with targeted immunotherapy is a promising approach in that RIT, like stereotactic body radiotherapy (SBRT), may stimulate a local immune response that can be boosted with targeted immunotherapy. In this respect, we have recently shown that SBRT plus a CEA targeted immunocytokine (ICK) gave superior tumor reduction than either monotherapy [20]. Those studies were performed with humanized anti-CEA antibody M5A [21] and an M5A-IL2 fusion protein [20]. We now extend those studies to the combination of targeted alpha-therapy (TAT) plus ICK. The choice of alpha-emitting radionuclide therapy over beta-emitting radionuclide therapy is based on the fact that alpha-emitters deliver more energy to their tumor target due to their high linear energy transfer [22] with a potential increase in tumor cytotoxicity due to stimulation of an immune response. In addition, their low tissue penetration is expected to reduce heme toxicity, one of the major off-target effects of beta-emitter based RIT [23]. For this study, we chose the alpha-emitter $^{225}$Ac for its long half-life (10 days) and emission of four alpha-particles [24]. We have previously investigated the use of TAT in the treatment of ovarian cancer [25] and multiple myeloma [26], finding that in one study, alpha-based TAT was superior to beta-based RIT [26].

Since we hypothesized that TAT was more likely than RIT to stimulate an immune response to tumors, we combined TAT with targeted immunotherapy to further boost the immune response. In order to test this hypothesis, it was necessary to perform these studies in immune competent mice that expressed the target antigen of interest. For this reason, we utilized CEA transgenic mice in which the entire human CEA gene was expressed, conferring tissue specific CEA expression that mimics that found in man [27]. We have previously shown that an all murine anti-CEA ICK reduced CEA positive tumor growth in this CEA transgenic model [28], and more recently, that an all murine anti-CEA CAR plus the humanized ICK reduced tumor growth in the same model [29].

Materials and Methods

M5A, ICK, and the cell lines E0771-CEA and MC38-CEA were previously described [30]. The primary antibodies used for immunohistochemistry were anti-human CEA antibody M5A, anti-human CD8 (Clone #SP57, Rabbit monoclonal antibody from Ventana), anti-mouse F4/80 (Clone #D2S9R, Rabbit monoclonal antibody from Cell Signaling), and anti-mouse CD31 (Clone #D8V9E, Rabbit monoclonal antibody from Cell Signaling).

Radiolabeling. M5A antibodies were reacted with a 30-molar excess of the chelator DOTA-NHS ester as previously described [31]. DOTA conjugation was confirmed by Q-TOF mass spectrometry (Agilent Technology 6510 QTOF LC/MS) as follows: 6 μg of antibody was reduced with 1 μL of 0.2 M Tris(2-carboxyethyl)phosphine (TCEP) for 2 hours at 37° C. and then analyzed on an HPLC protein Agilent chip (Agilent Technologies, Santa Clara, CA). DOTA-conjugated antibody (50 μg) was incubated with $^{225}$Ac at a labeling ratio of 1.85 MBq/μg for 45 min at 43° C., and chased with 1 mM DTPA. Radiolabeling efficiencies determined by instant thin layer chromatography [32].

Immunohistochemistry (IHC) was carried out by the pathology core at City of Hope using the Ventana Discovery Ultra autostainer (Ventana Medical Systems, Roche Diagnostics, Indinapolis, USA) and the ChromoMap DAB detection system according to manufacturer's recommendations. Briefly, the tissue samples were collected and fixed in 4% paraformaldehyde for 3 days and then stored in 70% EtOH. The sampled were blocked in paraffin, sectioned at a thickness of 5 μm and put on positively charged glass slides. For hematoxylin & eosin (H&E) stains, the slides were deparaffinized, rehydrated and stained with Modified Mayer's Hematoxylin and Eosin Y Stain (America MasterTech Scientific) on a H&E Auto Stainer (Prisma Plus Auto Stainer, SAKURA) according to standard laboratory procedures. For the specific immunohistochemistry stains, the slides were loaded on the machine, deparaffinization, rehydration, endogenous peroxydase activity inhibition and antigen retrieval were first performed. Then, each primary antibody was incubated following by DISCOVERY anti-Rabbit HQ and DISCOVERY anti-HQ-HRP incubation. The stains were visualized with DISCOVERY ChromoMap DAB Kit, counterstained with hematoxylin (Ventana) and coverslipped. For humanized anti-human M5A antibody stains, Goat anti-human IgG antibody (H+L), biotinylated (Vector Laboratories) was used and followed by VECTOASTAIN ABC kits (HRP) and DAB. H&E or IHC stained slides were digitalized and documented by iScan HT (Roche) scanner.

All animal handling was done in accordance with IACUC protocol 14043 and 91017 approved by the City of Hope Institutional Animal Care and Use Committee. CEA transgenic mice were previously described [27]. The E0771-CEA cells were injected into the mammary fat pad, 1E5 cells per mouse in Matrigel:PBS (1:1). In the TAT alone treated E0771 group, 1E5 E0771 cells were injected into the mammary fat pad at day 0. TAT was given 8 days later, with the early time point collection 21 days post E0771 injection. In the combinatorial studies, either ICK or 7.4 kBq TAT was given on day 8 post E0771 injection, with ICK given once daily for 4 days at a 1 mg/kg dose. In the combination groups, TAT was given at day 13, following the last dose of ICK, or after TAT, ICK was started on day 18, following the same once daily for four days dosing regimen. The early time point collection was at day 21 post E0771 injection, while the late time point was collected at the end point for each mouse. In the E0771 experiments examining the timing to give ICK, TAT was given on day 8, followed by the ICK regimen starting on day 13 (5 days post TAT) or at 18 days (10 days post TAT).

The MC38-CEA cell line was injected subcutaneously (SQ), 1E6 cells per mouse. In the TAT alone treated MC38 experiment, 1E6 cells were injected subcutaneously at day 0. The mice were treated with 3 dose levels of TAT 13 days later, with blood collected for hematological analysis at end point. In the combinatorial studies, ICK or TAT alone was given starting at day 13 post MC38 engraftment, followed by the ICK regimen starting 10 days later. The early time point collection was 27 days post MC38 injection, while the late time point was collected at the end point for each mouse. This preliminary 27 day early time point was to soon for the collection of tissues for flow analysis, so this experiment was repeated collecting tissues to measure the infiltration of the immune cells into the tumor and their expansion in the spleen. In the repeat dosing experiment, SQ MC38 was treated 13 days later with either 2 doses of 7.4 kBq TAT, given 10 days apart, or one dose of 14.8 kBq TAT. Plasma and tumor tissue were collected at the end point. The tumor size was followed by caliper measurements (TS=0.5(L×W2)). Toxicity was measured by monitoring weight loss of the mouse, with >20% weight loss considered an endpoint. Collections were done at the endpoint for flow, IHC, heme analysis, and kidney and liver toxicity.

Toxicity analysis. Hematologic analysis was done using the VETSCAN HM5 Hematology Analyzer. Blood (50-100 μl) was collected and stored in EDTA tubes until analyzed, 1-2 hours post collection. For kidney and liver toxicity, about 400 ul blood was collected in lithium heparin tubes and spun down to separate RBCs and plasma. Plasma was collected and stored at −80C until analysis on the VETSCAN VS2 Chemistry Analyzer, using the Preventive Care Profile Plus rotors (Zoetis).

Leukocyte analysis. Tissues and blood were collected at the termination of the studies and leukocyte populations were analyzed by flow cytometry. Blood samples were used after red cells lysis. Tumor draining lymph nodes and spleens were pushed through a 40 μm cell strainer and red cells were lysed. Lungs and tumors were dissociated by enzymatic digestion using gentleMacs Octo Dissociator and dissociation kit following the manufacture's protocol (Miltenyi Biotec). Cell suspensions were stained with different combinations of fluorochrome-coupled antibodies to CD3, CD4, CD8, B220, CD19, CD11b, Ly6C, Ly6G, CD11c, F4/80, NK1.1, NKp46, PD-1, CTLA-4, Tim-3 (BioLegend). For IFNγ production cells from all tissues were re-stimulated using PMA (10 ng/ml; Sigma-Aldrich) and ionomycin (1 μg/ml; Sigma-Aldrich) in the presence of Brefeldin A (5 μg/ml; BioLegend, CA) in 10% FBS IMDM media for 4 hours in 37° C. Next, cells were stained for surface markers and viability marker (Zombie UV, BioLegend) and fixed and permeabilized using Foxp3 Transcription Factor Fixation/Permeabilization kit (ThermoFisher) following the manufacture's protocol. Finally, cells were stained for intracellular IFNγ (BioLegend) and analyzed by flow cytometry. For FoxP3 (ThermoFisher) expression cells were stained for surface markers, fixed and permeabilized as described above.

For statistical analysis of the in vivo efficacy studies, two-way ANOVA (Tukey's multiple comparison test) was used to analyze the tumor growth curves, using Prism 8.3.0 (GraphPad Software). The test compared each group to the untreated saline control group. The log-rank Mantel-Cox test was used to analyze the survival curves. Survival was defined as the time in which the tumor reached 1500 $mm^3$. Each treated group was compared to the saline control group, unless otherwise stated. Differences were considered significant if P50.05.

Results

Figure 1C:
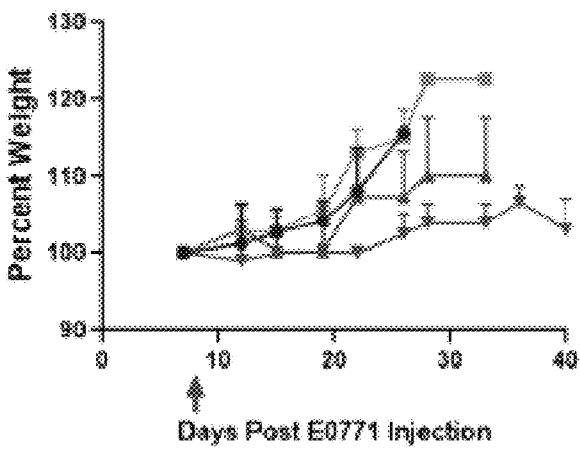

Targeted alpha therapy (TAT) of CEA positive mammary tumors. Murine mammary cancer cells E0771 transfected with CEA [30] were injected into the mammary fat pad of CEA transgenic mice [27] to establish mammary tumors in a immunocompetent model that expressed the human CEA gene. Since we have previously shown that these tumors do not respond to humanized anti-CEA antibody M5A [30], we tested their response to TAT with $^{225}$Ac-DOTA-M5A. Increasing doses from 3.7 kBq to 11.1 kBq show a dose response with the highest dose leading to a delay in tumor growth of about 30 days (FIG. 1A) and an increase in median survival (defined as maximum tumor size>1500 $mm^3$) from 20 days to 36 days (Table 2, FIG. 2B). Whole body toxicity as measure by weight loss (≥20% loss was considered toxic) was minimal at all doses (FIG. 1C). In addition, reduction of platelet and neutrophil counts were transient and there was no evidence of liver or kidney toxicity measured at the end of the study (Table 1).

TABLE 1

| | BUN (mg/dL) | CRE (mg/dL) | ALT (U/L) | AST (U/L) |
|---|---|---|---|---|
| Murine Normal | 22.1 ± 5.3 | 0.5 ± 0.17 | 40 ± 20.6 | 140.6 ± 67.4 |
| Saline* | 23.5 | 0.30 | 36.4 | 266 |
| 3.7kBq of $^{225}$Ac-M5A | 22 | 0.45 | 39 | 352 |
| 7.4kBq of $^{225}$Ac-M5A* | 24.1 | 0.30 | 41, 41 | 405, 304 |
| 11.1kBq of $^{225}$Ac-M5A | 25 | 0.50 | 41 | 369 |
| ICK | 26.3 | 0.3 | 34.3 | 168.3 |
| ICK + 7.4kBq TAT | 20.7 | 0.2 | 36.7 | 292 |
| 7.4kBq TAT + ICK | 25 | 0.2 | 46 | 303 |

For Table 1: Kidney/Liver Toxicity associated with Combination TAT and ICK Therapy in a Breast Cancer Model. Liver Toxicity: alanine aminotransferase (ALT)/aspartate aminotransferase (AST); Kidney Toxicity: Blood Urea Nitrogen (BUN)/creatinine (CRE). Plasma analyzed at end point of each mouse. N=4, N*=4+4$^+$. . . *=average of all groups. For murine normal, see Harrison et al, Cancer Research, 38:2636-2639 (1978).

TABLE 2

| | Saline* | 3.7 kBq TAT | 7.4 kBq TAT* | 11.1 kBq TAT | ICK | ICK + 7.4 kBq TAT | 7.4 kBq TAT + ICK(18 d)* | 7.4 kBq TAT + ICK(13 d) |
|---|---|---|---|---|---|---|---|---|
| Median Survival | 21.8 | 24.0 | 28.9 | 36.0 | 31.2 | 30.2 | 43.7 | 45.4 |

Figure 1D:
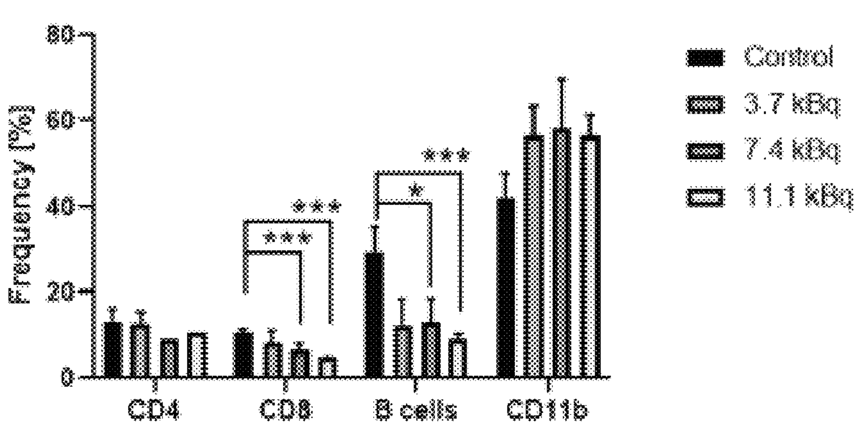
Figure 1E:
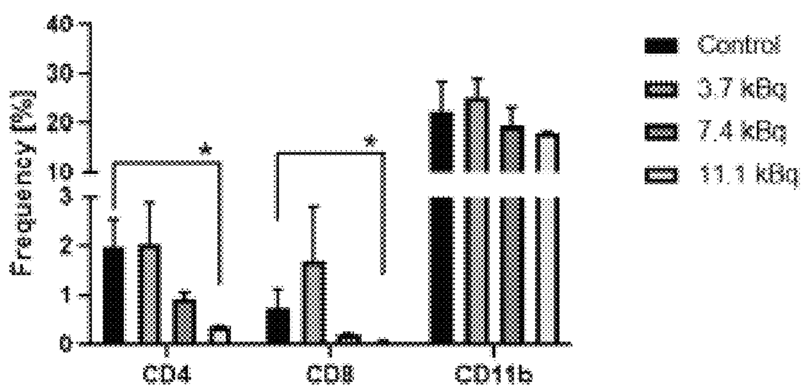
Figure 1F:
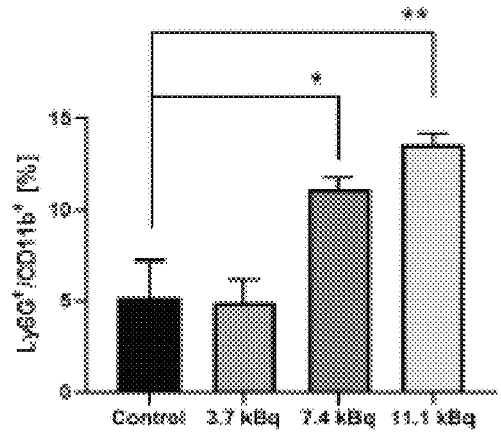

Flow cytometry analysis of the blood at day 21 indicated a significant decrease of CD8 T-cells and B cells for the two highest doses of TAT with no effect of CD11b myeloid cells (FIG. 1D). The highest dose of TAT significantly reduced tumor infiltration of both CD4 and CD8 T-cells (FIG. 1E) and an increase of tumor infiltrating neutrophils by 7.4 kBq and 11.1 kBq TAT (FIG. 1F). These results suggest the possibility that TAT had a major effect on the immune response to the tumor, but it was unclear if the effect was immunosuppressive or stimulatory.

Figure 2A:
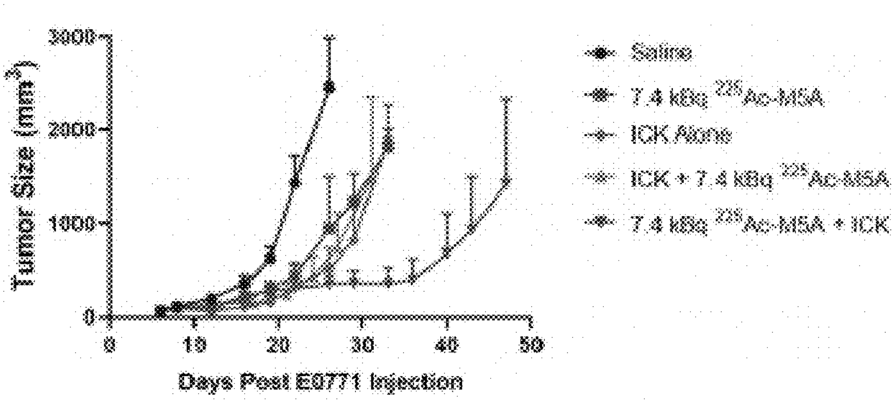
Figure 2B:
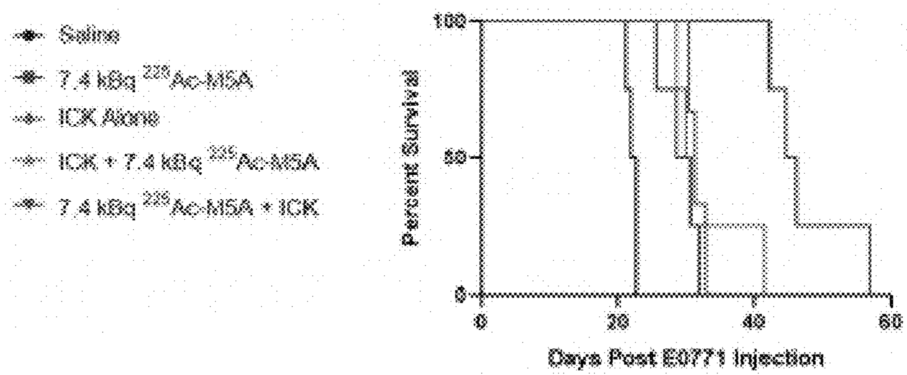

Combined TAT plus immunocytokine (ICK) therapy of CEA positive mammary tumors. Since we had previously shown that antibody targeted IL2 therapy with the immunocytokine anti-CEA antibody M5A-IL2 was able to delay tumor growth in the E0771/CEA CEA transgenic mouse model [30], we tested the ability of combined TAT plus ICK to determine if ICK therapy would be adversely affected by TAT. The ICK therapy schedule of 4 daily doses at 1 mg/kg starting at day 8 after tumor inoculation into the mammary fat pad adopted from our previous study [30], gave a significant delay of tumor growth of about 20 days compared to untreated tumors (FIG. 2A, red curve). Interestingly, the delay in tumor growth for ICK therapy alone was equivalent to the middle dose of 7.4 kBq of TAT only (FIG. 2A, green curve). When ICK was given prior to TAT (FIG. 2A, orange curve), the results were similar to either monotherapy. Thus, we next tested the combination of TAT followed by ICK. Given the 2-4 day half-life of the circulating antibody in the blood [33] and the 10 day half-life of $^{225}$Ac, we chose 10 day post TAT to allow for a reduction in the deleterious effects of circulating $^{225}$Ac-DOTA-M5A. When the combination of TAT plus ICK in which TAT was followed by ICK 10 days later, tumor growth was reduced to 38 days (FIG. 2A, purple curve) with an increase in median survival to 45 days compared to either monotherapy of 30 days (Table 2, FIG. 2B). Combination therapy did not result in significant whole body, heme, liver or kidney toxicity (Table 1, FIG. 12).

Figure 2C:
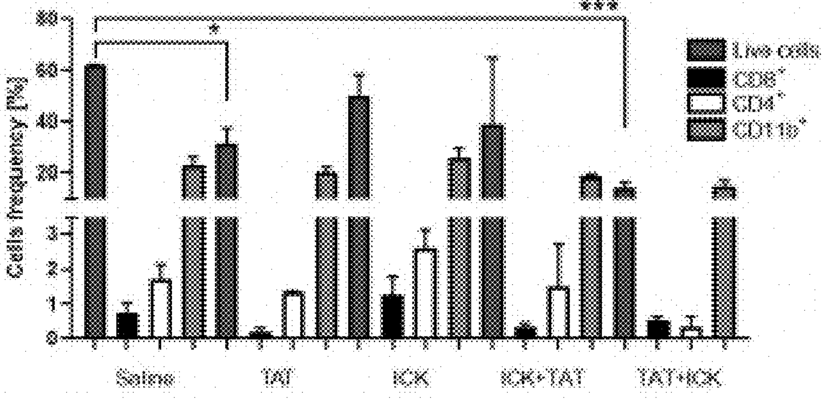
Figure 3A:
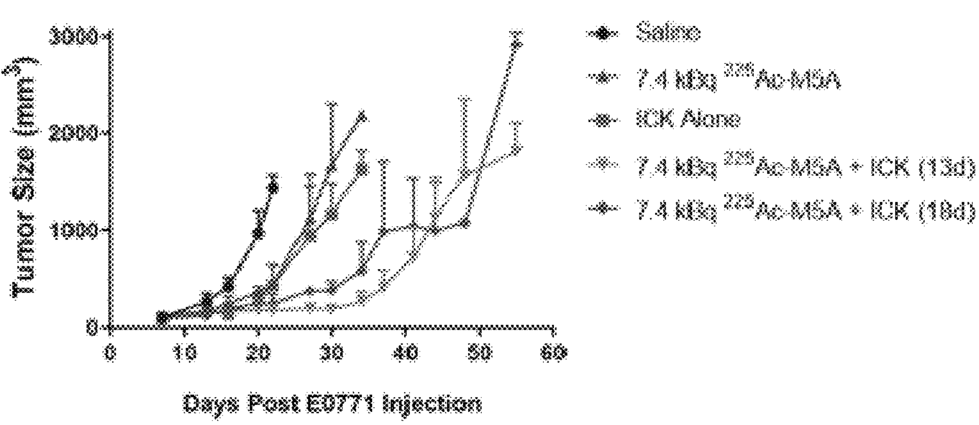
FIGS. 3A-3F are directed to experiments determining timing of ICK following 7.4 kBq $^{225}$Ac-M5A therapy. TAT was given day 8 post E0771CEA injection, followed by ICK treatment starting on day 13 or day 18.
Figure 3B:
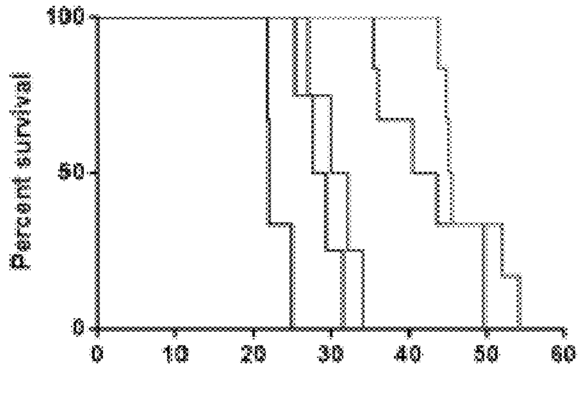
Figure 3C:
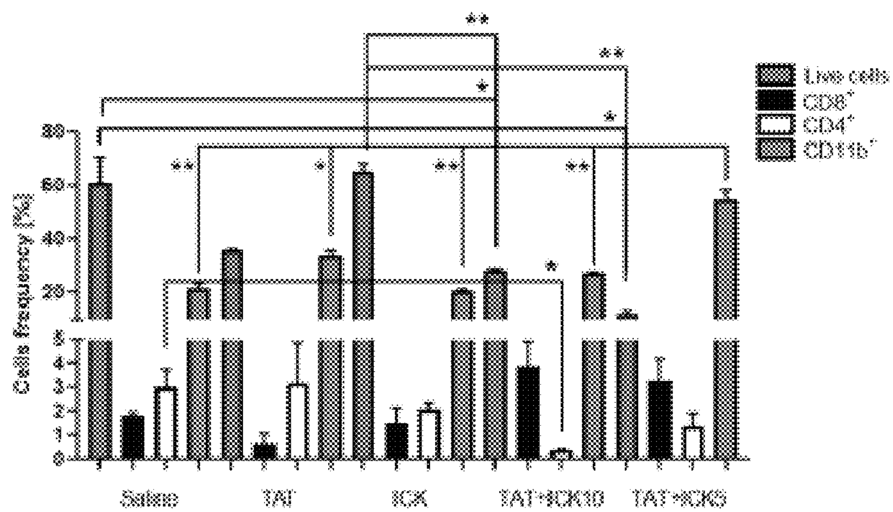
Figure 3D:
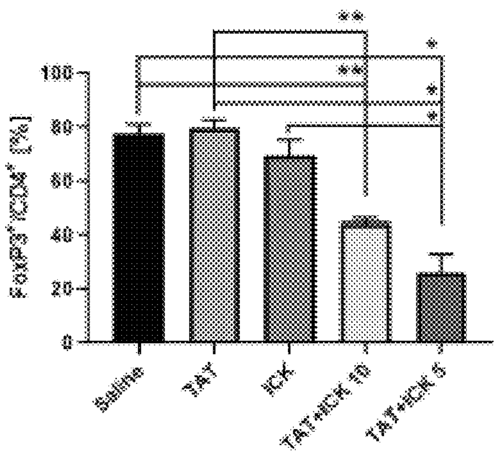
Figure 3E:
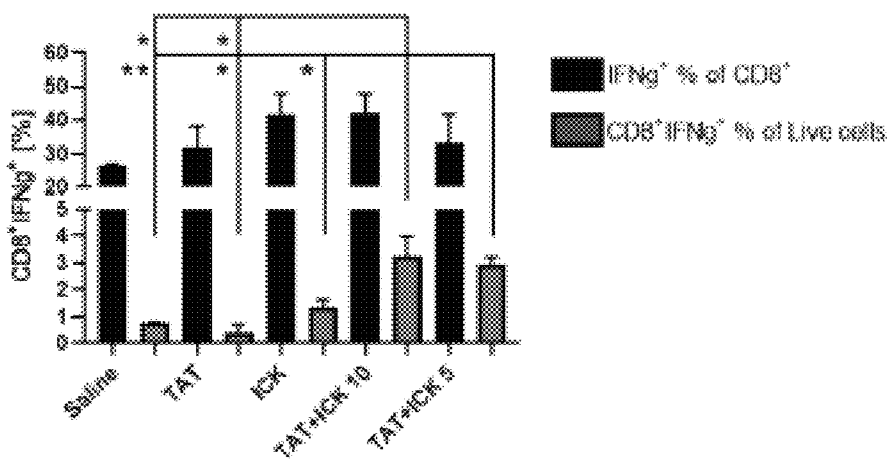
Figure 3F:
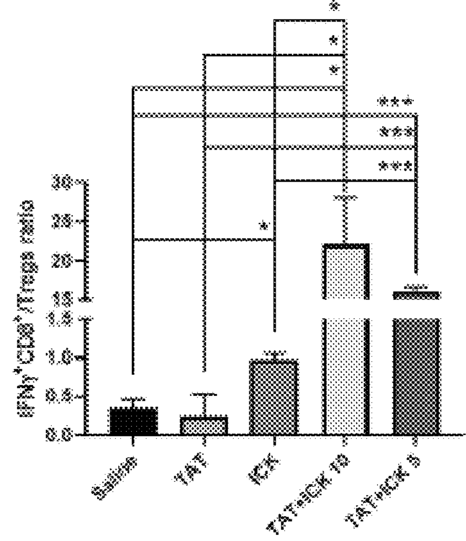
Figure 4A:
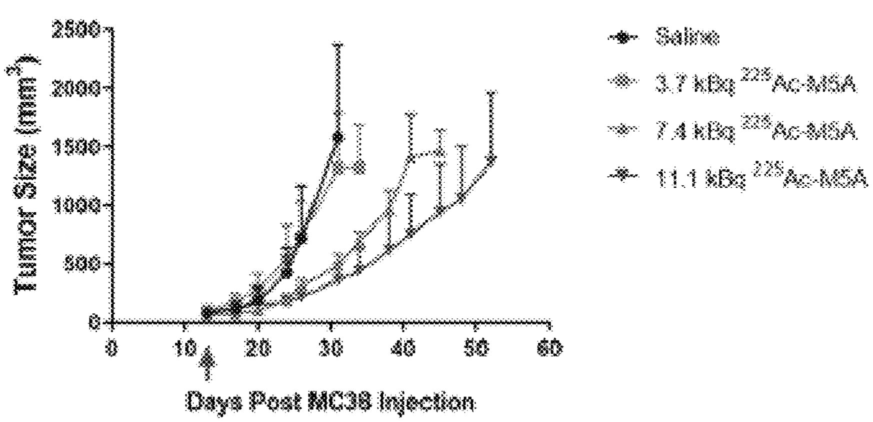
FIGS. 4A-4D show TAT therapy of murine MC38CEA colon carcinoma in a single dose escalation study and multidose approach.
Figure 4B:
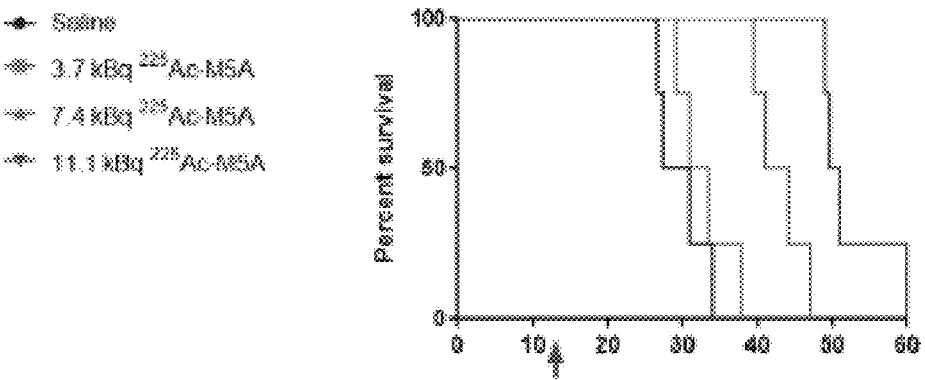
Figure 4C:
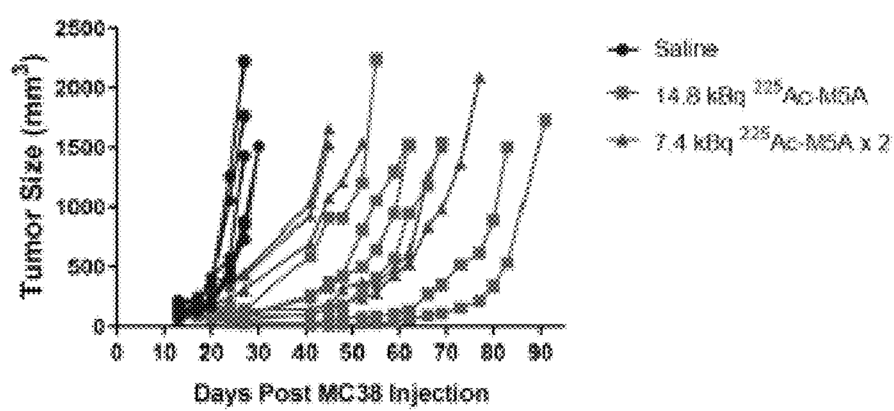
Figure 4D:
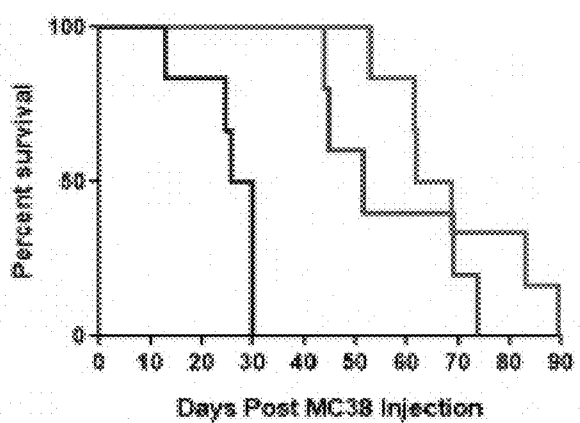

TAT therapy alone or in combination ICK affected the cellular viability of treated tumors at day 21 days as shown by flow cytometry (FIG. 2C). Although tumor infiltrating CD4 and CD8 cells were reduced by combined therapy, there was a significant increase of tumor infiltrating IFNγ$^+$ CD8$^+$ T-cells at day 21 (FIG. 2D) of which IFNγ$^+$PD-1$^+$ tumor infiltrating CD8$^+$ also increased (FIG. 2E). However, the ratio of CD8$^+$IFNγ$^+$ to CD4$^+$ Treg cells increased in both the ICK only and combined therapy groups, suggesting that the Tregs play more important role in the tumor response than the percentage of PD1$^+$CD8$^+$ T-cells. This analysis confirmed that TAT followed by ICK was superior to ICK followed by TAT, suggesting that TAT adversely affected ICK first in combination therapy, Timing of TAT plus IC combination therapy. Given the finding that TAT can adversely affect ICK therapy when ICK is given first but not when ICK was given 10 days after TAT, we tested the possibility of administrating ICK 5 days post TAT. Although the tumor reduction and survival curves showed slight differences between ICK 5 days vs 10 days after TAT, overall the results were statistically identical (FIG. 3A-3B). Flow analysis of infiltrating leukocytes in the tumor were also similar between the two combination therapy groups (FIG. 3D-3F). Of special interest, the percent CD4$^+$Foxp3$^+$ Tregs and their ratio to IFNγ$^+$CD8$^+$ cells was higher in the +10 day group vs the +5 day ICK group (FIG. 3D-3F). We surmise that delaying ICK after TAT is beneficial in combination therapy when tumor growth is retarded and can be given as early as 5 days post TAT.

Combined TAT plus immunocytokine (ICK) therapy of CEA positive colon tumors. To confirm the efficacy of combined TAT plus ICK therapy in a second tumor model, we chose CEA transfected murine colon carcinoma MC38 cells engrafted s.c. in CEA transgenic mice. There was a dose response of 3.7-11.1 kBq in a TAT only study (FIG. 4). At the lowest dose (3.7 kBq), there was little difference in tumor reduction or survival between control and treated tumors (FIGS. 4A-4B, curves formed by circles vs squares), but at the middle (7.4 kBq) and highest (11.1 kBq) dose, there was a significant reduction in tumor growth and increase in survival. Since the lowest dose had little effect on tumor growth, it is likely that these tumors are more radiation resistant than the E0771 mammary tumors. Therefore, we considered increasing the dose in two ways, first by doubling the maximum dose to 14.8 kBq, and second, by administering the 7.4 kBq dose twice, once at 13 day post tumor inoculation and again 10 days later. The tumor growth curves for individual mice shown in FIG. 4C reveal an interesting spread in response to TAT, suggesting that minor differences in tumor sizes or microenvironment affect the response to TAT that are not apparent in the control tumors. However, both the tumor growth and survival curves (FIG. 4D) indicate that the single 14.8 kBq dose is superior to the fractionated 2×7.4 kBq dose.

Figure 5A:
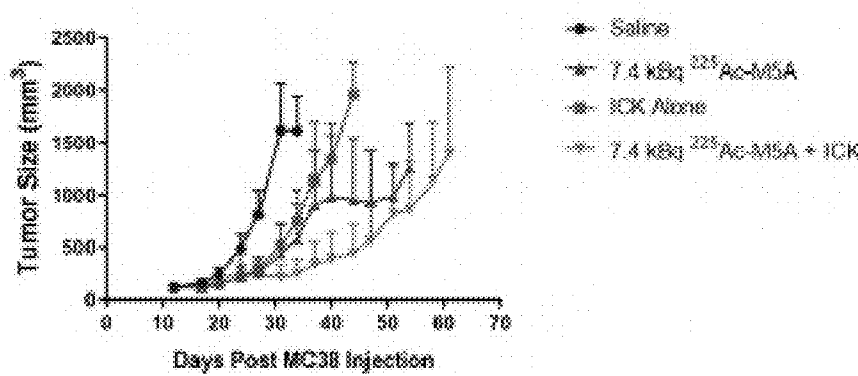
Figure 5B:
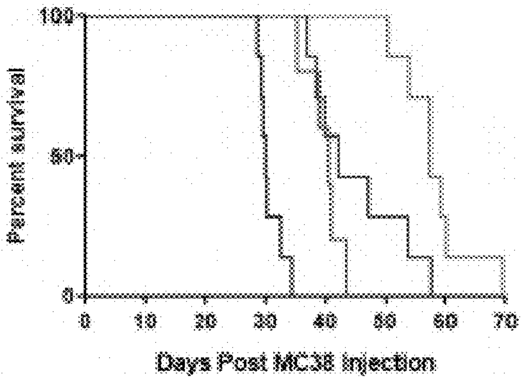

In order to directly compare the two tumor model responses to combined therapy, the identical TAT dose of 7.4 kBq was chosen with a delay of 10 days for the start of ICK. The tumor growth curves for TAT or ICK monotherapy were identical until 35 days after which ICK monotherapy showed tumor escape (FIG. 5A, curves formed by squares vs triangles). From day 35 to day 50, TAT only showed a plateau, suggesting that TAT only may have generated a transient host immune response. However, the combined therapy showed an improved tumor growth reduction out to about 45 days after which tumor escape became obvious (FIG. 5A, orange curve). In terms of median survival, the combination therapy was 57 days vs 30 days for untreated controls (Table 4, FIG. 5B). Although the survival curves showed differences between the two monotherapies, their median survivals were similar. No whole body or significant heme, liver or kidney toxicities were noted in this tumor model (Table 3, FIGS. 15-16).

TABLE 3

| | BUN (mg/dL) | CRE (mg/dL) | ALT (U/L) | AST (U/L) |
|---|---|---|---|---|
| Murine Normal | 22.1 ± 5.3 | 0.5 ± 0.17 | 40 ± 20.6 | 140.6 ± 67.4 |
| Saline | 31 | .25 | 24.5 | 198 |
| 7.4kBq of $^{225}$Ac-M5A x2 | 27.5 | .25 | 35 | 185 |
| 14.8kBq of $^{225}$Ac-M5A | 24 | .3 | 36.5 | 154 |

For Table 3: Kidney/Liver Toxicity associated with TAT in a Colon Cancer Model. Liver Toxicity: alanine aminotransferase (ALT)/aspartate aminotransferase (AST); Kidney Toxicity: Blood Urea Nitrogen (BUN)/creatinine (CRE). Plasma analyzed at end point of each mouse. N=4. For murine normal, see Harrison et al, Cancer Research, 38:2636-2639 (1978).

TABLE 4

| | Saline* | 3.7 kBq TAT | 7.4 kBq TAT* | 11.1 kBq TAT | ICK | 7.4 kBq TAT + ICK | 7.4 kBq TAT × 2 | 14.8 kBq TAT |
|---|---|---|---|---|---|---|---|---|
| Median Survival | 29.1 | 32.2 | 42.3 | 50.2 | 40.6 | 57.3 | 51.5 | 65.3 |

Figure 5F:
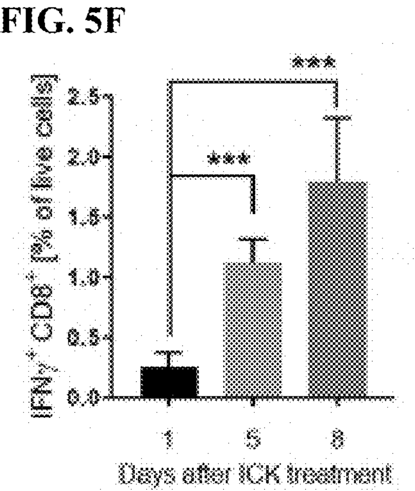
Figure 5G:
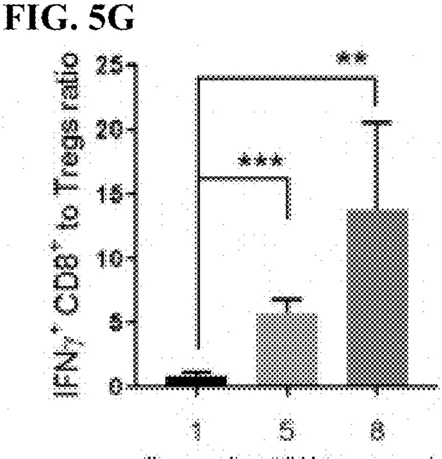
Figures 6A, 6B, 6C, 6D, 6E, 6F, 6G, 6H:
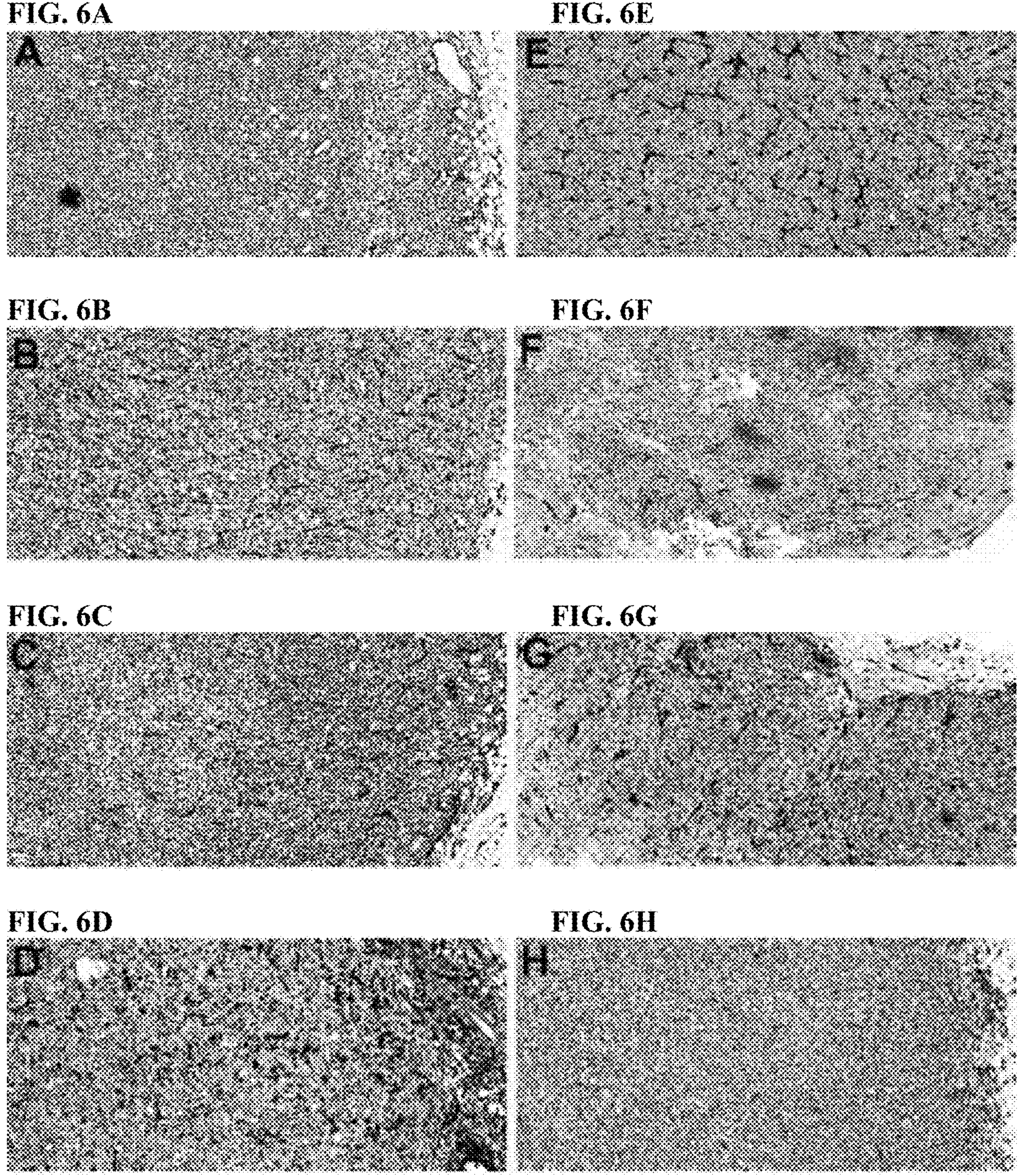
FIGS. 6A-6H show immunohistochemistry analyses.
Figures 7A, 7B, 7C, 7D, 7E, 7F, 7G, 7H:
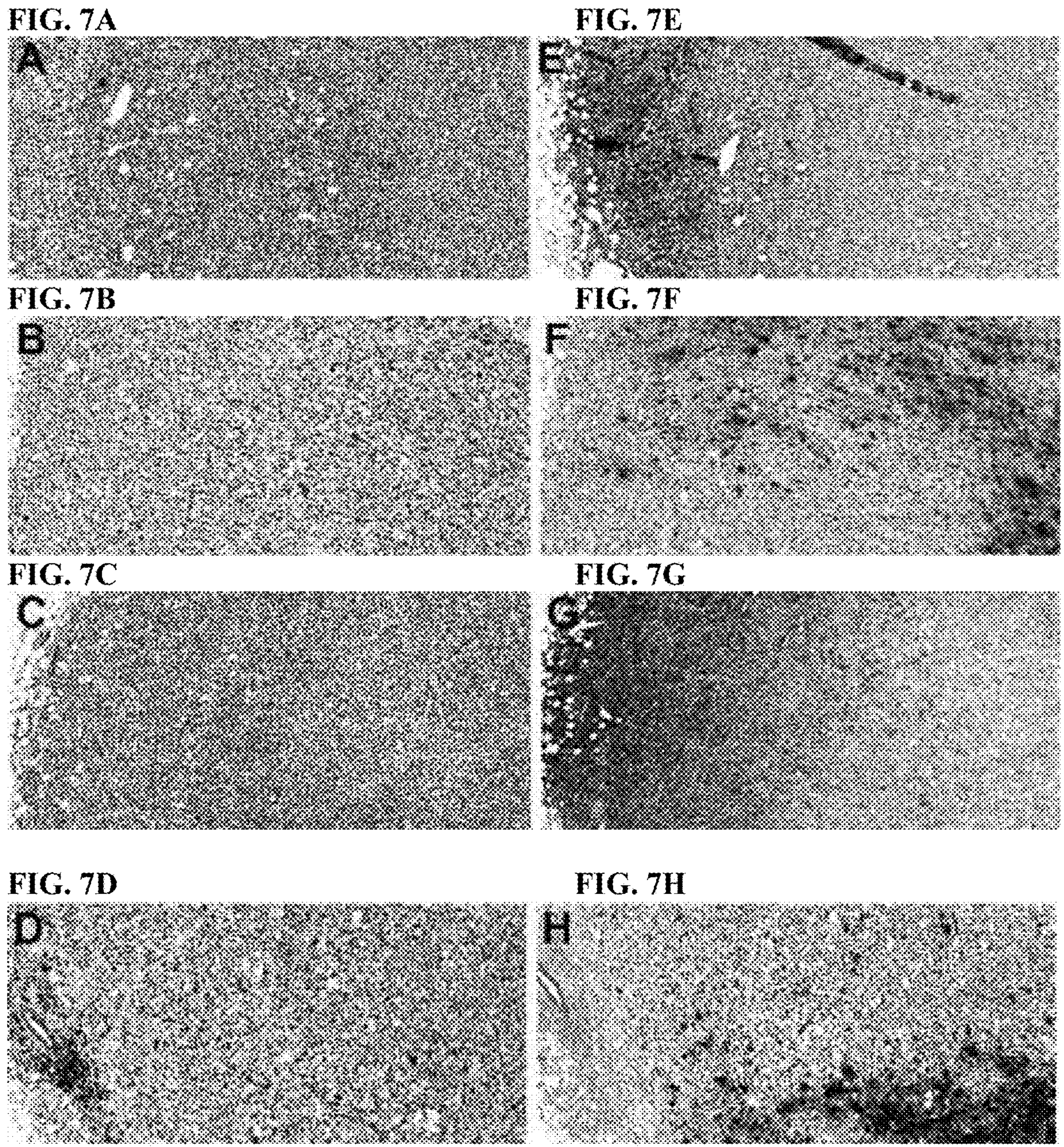
FIGS. 7A-7H show immunohistochemistry analyses. CD8 numbers were low in both untreated control and TAT only E0771/CEA treated breast cancer tumors, increased remarkably in ICK only treated tumors, and returned to low numbers in combined therapy (FIGS. 7A-7D). CEA expression was largely limited to the tumor periphery in untreated controls and was markedly decreased towards the tumor center (FIG. 7E). TAT only therapy greatly reduced CEA expression at the tumor periphery while preserving expression towards the tumor center (FIG. 7F), while the opposite was true for ICK only therapy (FIG. 7G). CEA expression in the combined therapy tumors was similar to TAT only therapy (FIG. 711).
Figures 8A, 8B, 8C, 8D:
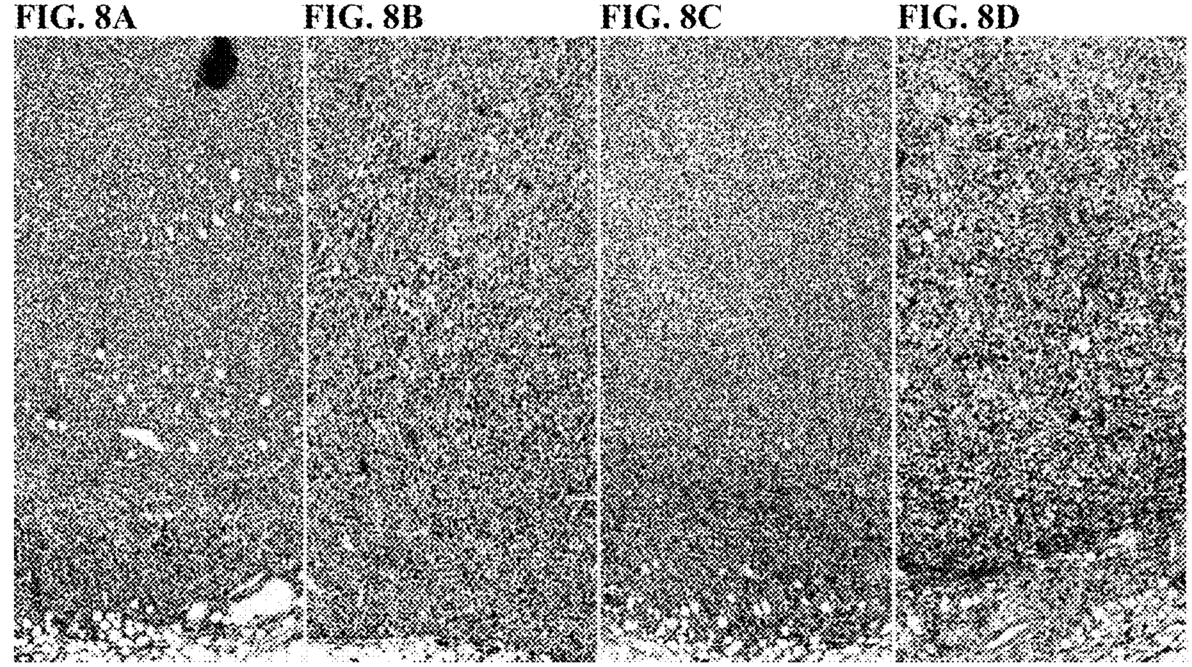
FIGS. 8A-8D show breast tumors stained for myeloid cells with the antibody F4-80 in untreated controls (FIG. 8A), TAT only (FIG. 8B), ICK only (FIG. 8C), and combination of TAT and ICK (FIG. 8D).

There was a significant increase of tumor infiltrating $CD4^+$ and $CD8^+$ T-cells in mice treated with ICK vs controls as analyzed by flow cytometry at day 27d (FIG. 5C). Both $IFN\gamma^+$ $CD4^+$ and $CD8^+$ T-cells were significantly increased by combination therapy (FIG. 5D). Tumors analyzed at days 1, 5 and 8 after the last dose of ICK in the combined therapy group shows a gradual increase of $CD8^+$ T-cells infiltration (FIG. 5E). The increase of tumor infiltrating $IFN\gamma^+$ $CD8^+$ T-cells at days 5 and 8 after the last dose of ICK in combined therapy group, was especially evident (FIG. 5F). As in the other combined therapy model, the change in the ratio of $IFN\gamma^+$ $CD8^+$ T-cells to regulatory T-cells at day 5 and 8 after last dose of ICK in the combined therapy group was significant (FIG. 5G). We conclude that both tumor models show a similar augmented response of ICK combined with TAT in which the increase in cytotoxic infiltrating T-cells and decrease in tumor Tregs are due to the addition of ICK.

Immunohistochemistry Analysis of Therapies.

A limited number of tumors were harvested 5-10 days after therapy to study tumor morphology, vascularity, CEA expression, and lymphocyte infiltration. In the orthotopic mammary tumor model, vascularity as measured by CD31 staining was most affected by combination therapy as evidenced by increased staining and vessel size especially at the tumor periphery (FIGS. 6A-6D). In the colon cancer model, the vascularity of untreated tumors showed even CD31 staining across the entire tumor that was greatly disrupted by TAT only, ICK only and combination therapies (FIGS. 6E-6H).

CD8 numbers were low in both untreated control and TAT only E0771/CEA treated breast cancer tumors, increased remarkably in ICK only treated tumors, and returned to low numbers in combined therapy (FIGS. 7A-7D). CEA expression was largely limited to the tumor periphery in untreated controls and was markedly decreased towards the tumor center (FIG. 7E), indicating an vivo effect on CEA expression in this tumor model. Interestingly, TAT only therapy greatly reduced CEA expression at the tumor periphery while preserving expression towards the tumor center (FIG. 7F), while the opposite was true for ICK only therapy (FIG. 7G). CEA expression in the combined therapy tumors was similar to TAT only therapy (FIG. 7H), indicating that TAT therapy was most efficient in killing CEA positive cells at the tumor periphery, a result that may be explained by the low tissue penetration of alpha particles. In addition, breast tumors were stained for myeloid cells with the antibody F4-80 (FIGS. 8A-8D). In this series, F4-80 staining was most intense at the tumor periphery and relatively unchanged for ICK only therapy. However, TAT greatly increased myeloid staining throughout the tumor, indicating that TAT mobilized myeloid infiltration.

Figures 9A, 9B, 9C, 9D, 9E, 9F, 9G, 9H:
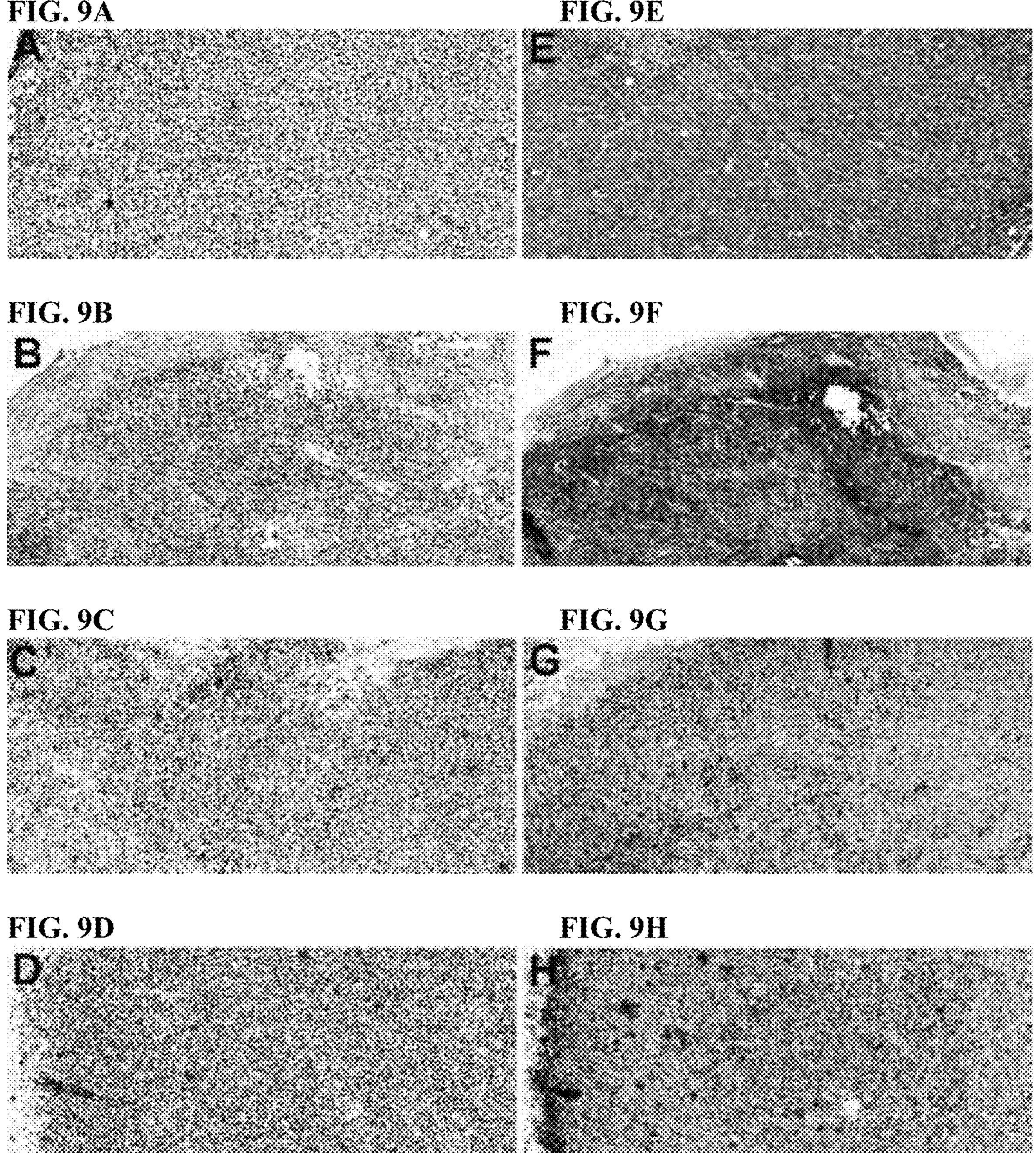
FIGS. 9A-9H show immunohistochemistry analyses. For CD8 staining of colon cancer tumors, untreated controls had large numbers of resident CD8 cells (FIG. 9A) that were greatly reduced by TAT only (FIG. 9B). The profile in ICK only therapy was intermediate with clusters of CD8 cells observed in regions of the tumor (FIG. 9C). Combination therapy was similar to TAT only (FIG. 9D). CEA staining was uniformly intense throughout the tumor in untreated controls (FIG. 9E), but with islands of low staining in TAT only tumors (FIG. 9F). Conversely, ICK only treated controls stained lightly for CEA with islands of CEA negative cells (FIG. 9G). The combined therapy tumors showed intense CEA staining at the periphery with a centralized area of less intense staining (FIG. 9H).
Figures 10A, 10B, 10C, 10D:
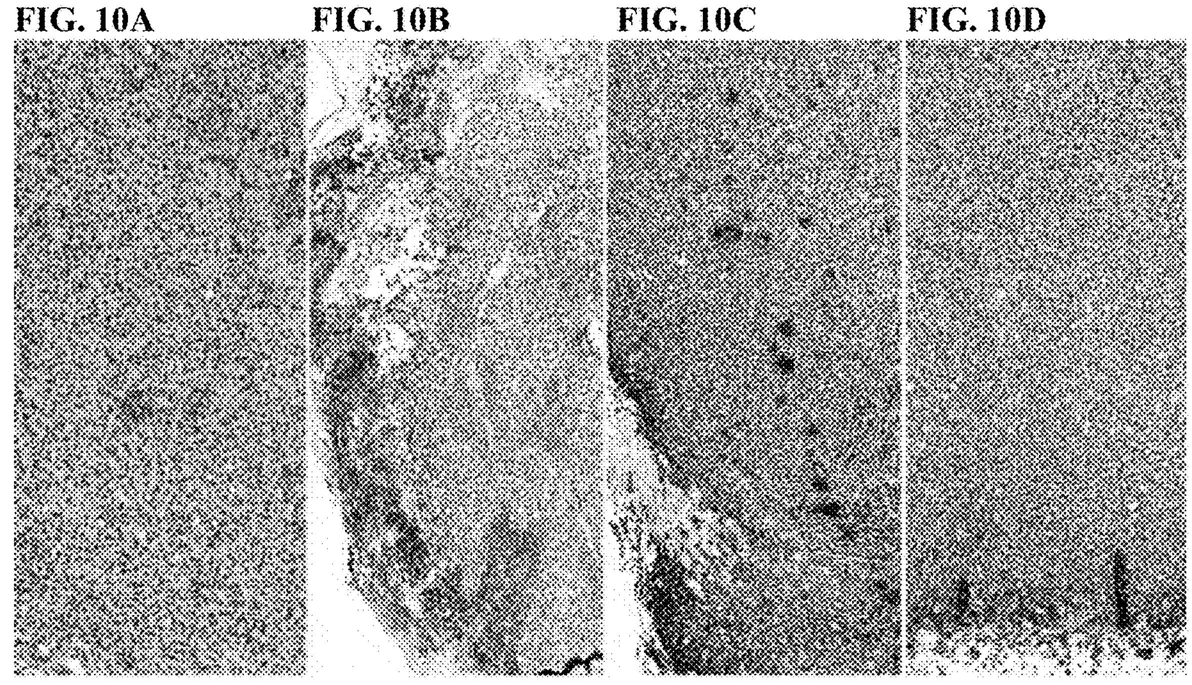
FIGS. 10A-10D show colon cancer tumors stained for myeloid cells with the antibody F4-80 in untreated controls (FIG. 10A), TAT only (FIG. 10B), ICK only (FIG. 10C), and combination of TAT and ICK (FIG. 10D).
Figure 11:
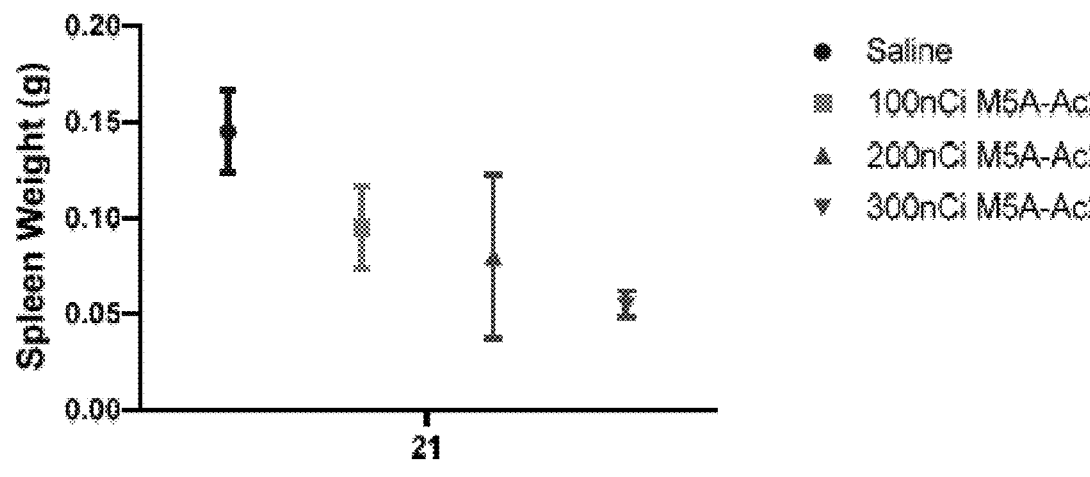
FIG. 11: E0771 Spleen weights. Tissue was collected and weighted. Early time point was collected 21 days post E0771 injection, N=2.
Figure 12A:
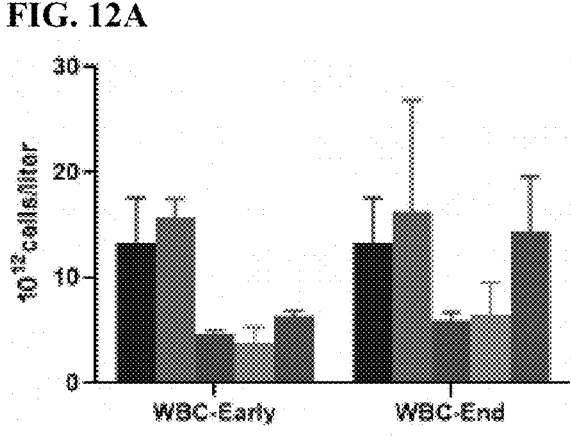
FIGS. 12A-12E show hematologic analysis of combination therapy in E0771 mice. Early time point was collected 21-22 days post E0771 injection, N=2. End time point was collected as each mouse reached the 1500 $mm^3$ end point, N=4.
Figure 12B:
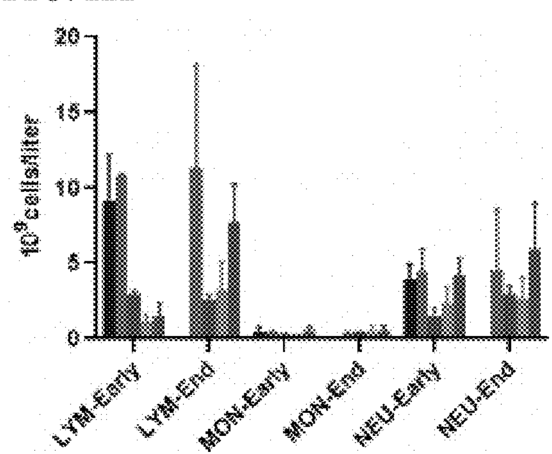
Figure 12C:
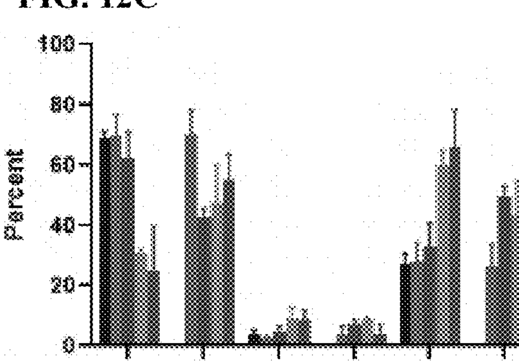
Figure 12D:
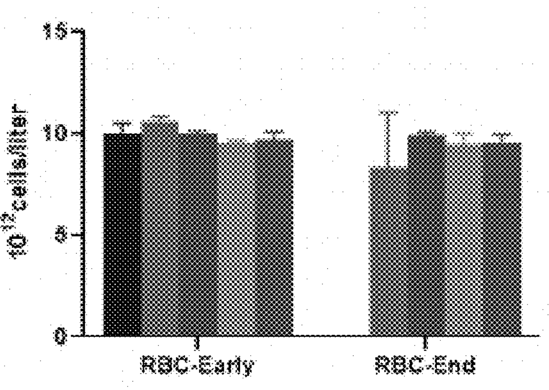
Figure 12E:
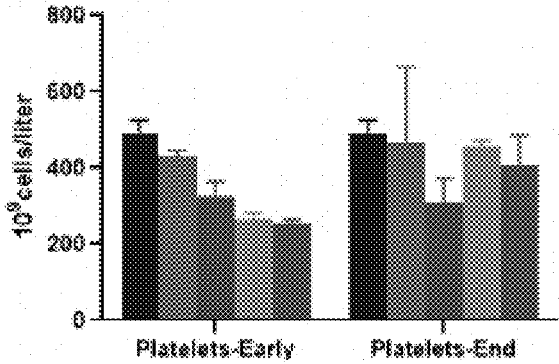
Figure 13A:
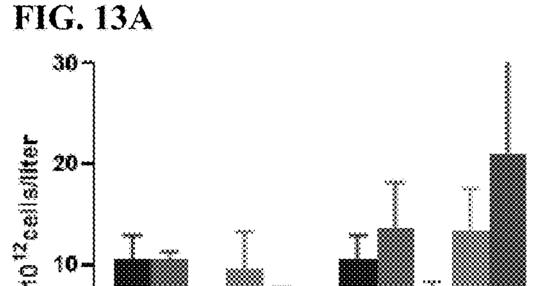
FIGS. 13A-13E show hematologic analysis of combination therapy in E0771 mice. Early time point was collected 22 days post E0771 injection, N=2. End time point was collected as each mouse reached the 1500 $mm^3$ end point, N=4.
Figure 13A:
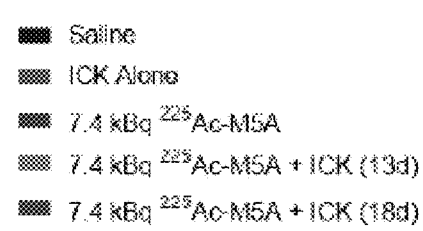
Figure 13B:
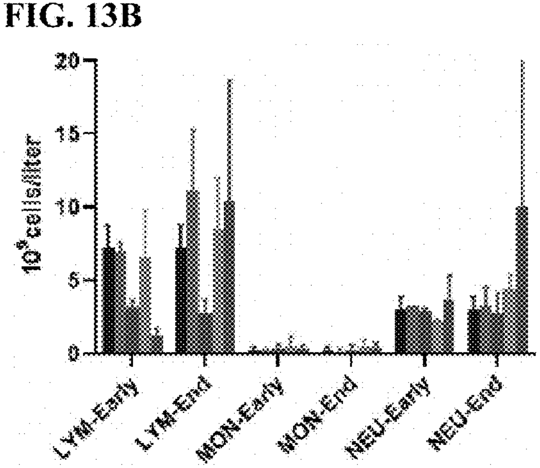
Figure 13C:
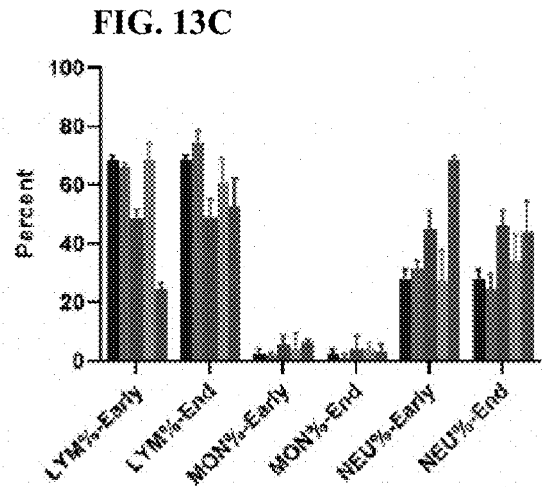
Figure 13D:
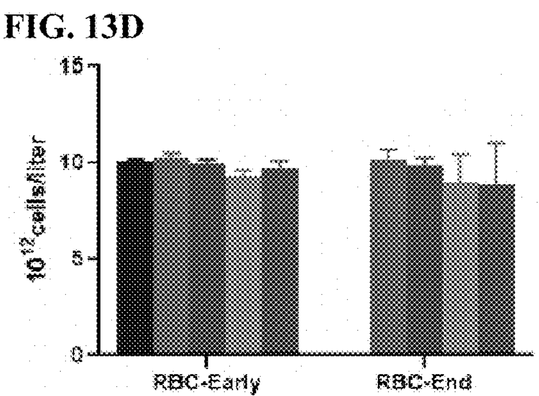
Figure 13E:
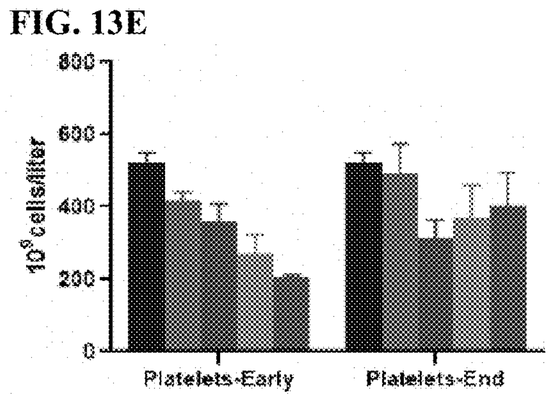
Figure 14:
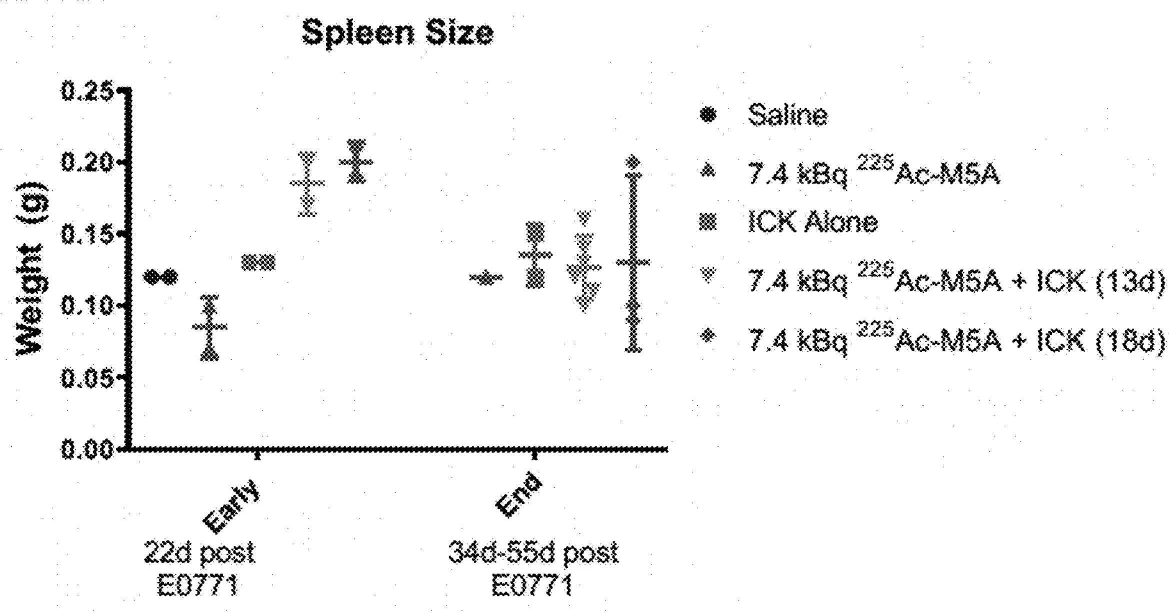
FIG. 14: E0771 Spleen weights. Tissue was collected and weighted. Early time point was collected 22 days post E0771 injection, N=2. End time point was collected as each mouse reached the 1500 $mm^3$ end point, N=4.
Figure 15A:
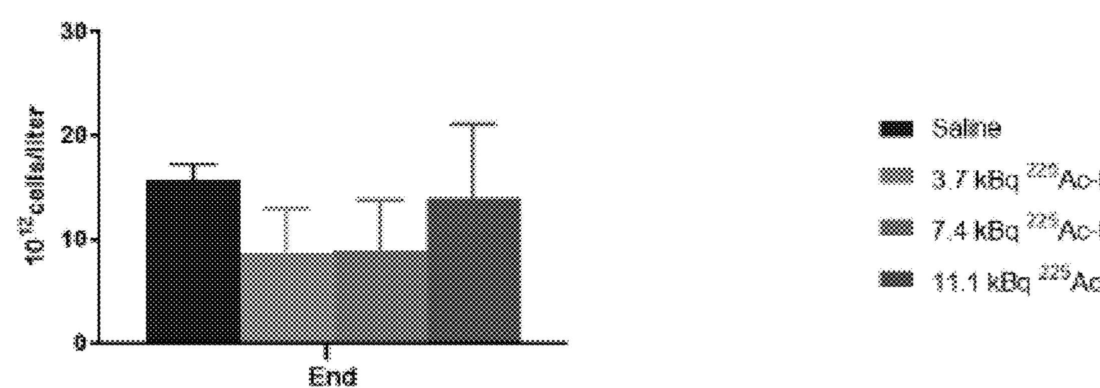
FIGS. 15A-15E: Hematologic Analysis of Dose escalation Study in MC38 engrafted mice. End time point was collected as each mouse reached the 1500 $mm^3$ end point, N=4.
Figure 15B:
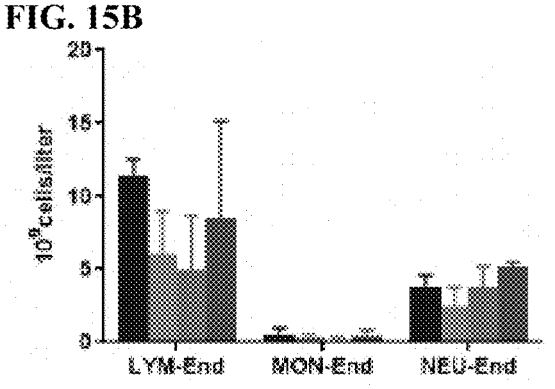
Figure 15C:
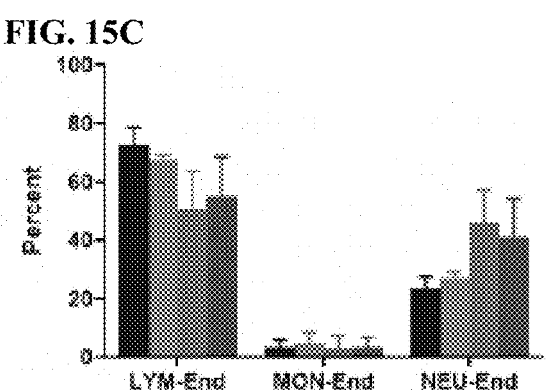
Figure 15D:
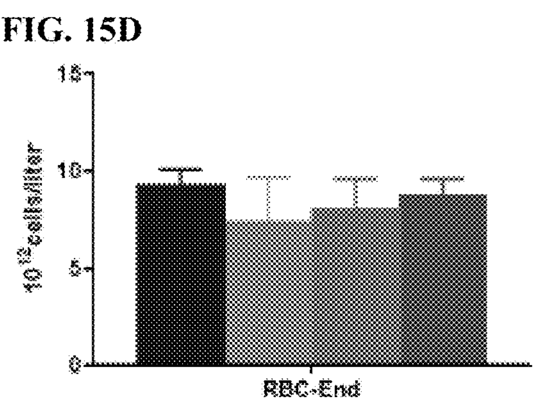
Figure 15E:
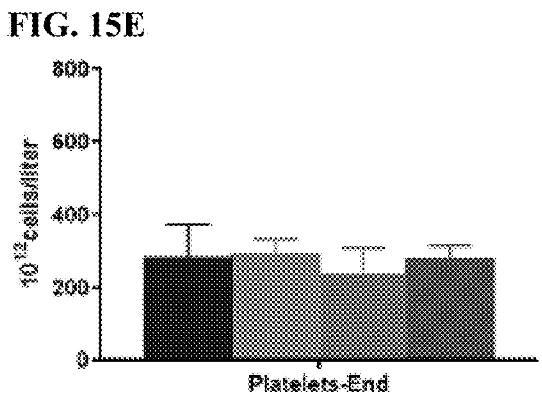
Figure 16A:
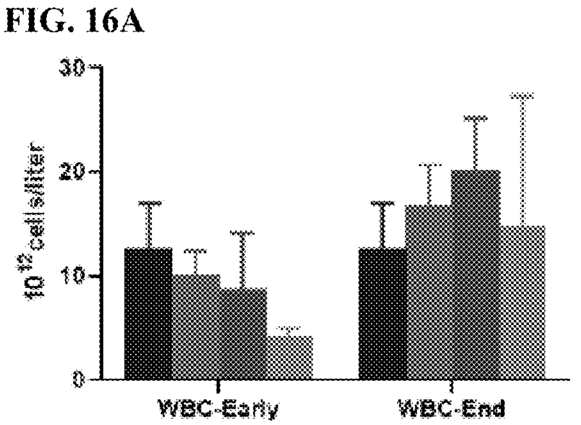
FIGS. 16A-16C: Hematologic Analysis of Combination Therapy Study in MC38 engrafted mice. Early time point was collected 22 days post E0771 injection, N=2-3. End time point was collected as each mouse reached the 1500 $mm^3$ end point, N=2-3.
Figure 16A:
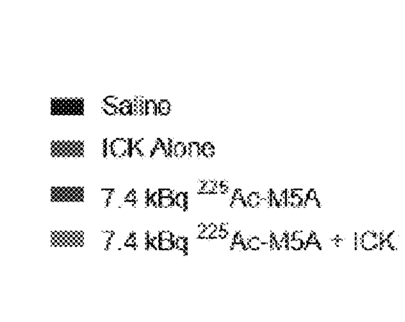
Figure 16B:
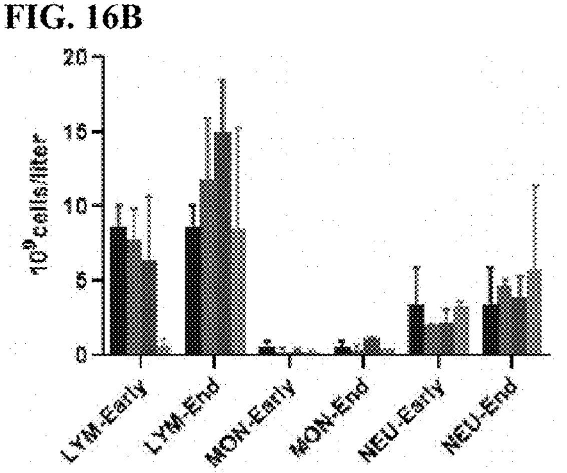
Figure 16C:
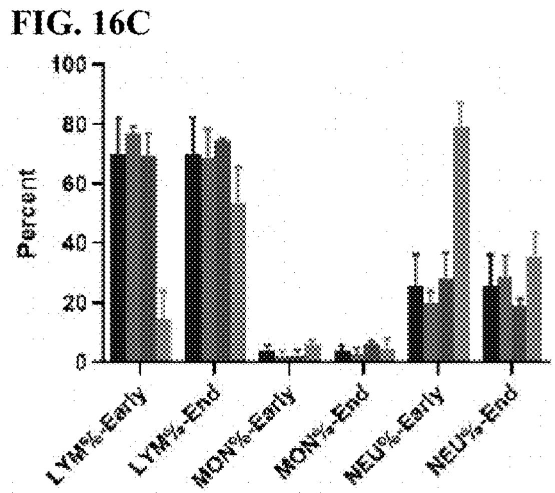
Figure 17:
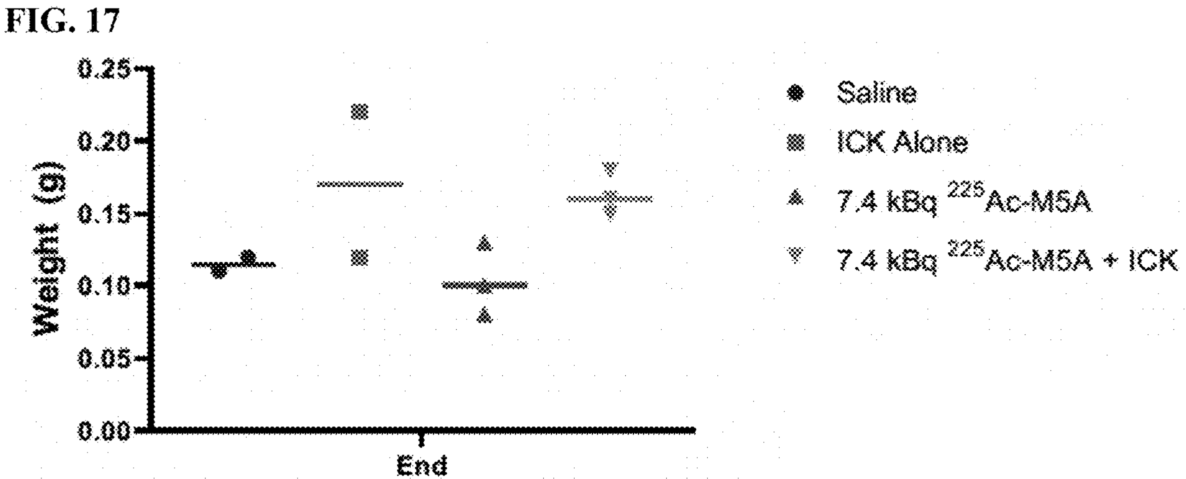
FIG. 17: Early Time Point of Spleen weights from Combination Therapy Study in MC38 engrafted mice. Spleens were collected at the early time point, 27d post MC38 injection.

For CD8 staining of colon cancer tumors, untreated controls had large numbers of resident CD8 cells (FIG. 9A) that were greatly reduced by TAT only (FIG. 9B). The profile in ICK only therapy was intermediate with clusters of CD8 cells observed in regions of the tumor (FIG. 9C), suggesting a redistribution and/or elimination of CD8 subtypes. Combination therapy was similar to TAT only (FIG. 9D). CEA staining was uniformly intense throughout the tumor in untreated controls (FIG. 9E), but with islands of low staining in TAT only tumors (FIG. 9F). Conversely, ICK only treated controls stained lightly for CEA with islands of CEA negative cells (FIG. 9G). The combined therapy tumors showed intense CEA staining at the periphery with a centralized area of less intense staining (FIG. 911). Myeloid cell staining with F4-80 exhibited a profile different from the mammary tumors with intense sporadic staining throughout the untreated controls changing to peripheral tumor staining in the TAT only, ICK only and combination treated tumors (FIGS. 10A-10D).

```
Informal Sequence Listing
SEQ ID NO: 1 = CDR-L1 of M5A and M5B
Arg Ala Gly Glu Ser Val Asp Ile Phe Gly

Val Gly Phe Leu His

SEQ ID NO: 2 = CDR-L2 of M5A and M5B
Arg Ala Ser Asn Leu Glu Ser

SEQ ID NO: 3 = CDR-L3 of M5A and M5B
Gln Gln Thr Asn Glu Asp Pro Tyr Thr

SEQ ID NO: 4 = CDR-H1 of M5A and M5B
Asp Thr Tyr Met His

SEQ ID NO: 5 = CDR-H2 of M5A
Arg Ile Asp Pro Ala Asn Gly Asn Ser Lys Tyr

Ala Asp Ser Val Lys Gly

SEQ ID NO: 6 = CDR-H3 of M5A and M5B

Phe Gly Tyr Tyr Val Ser Asp Tyr Ala Met Ala

Tyr

SEQ ID NO: 7 = CDR-H2 of M5B
Arg Ile Asp Pro Ala Asn Gly Asn Ser Lys Tyr

Val Pro Lys Phe Gln Gly

SEQ ID NO: 8 = variable light
chain domain of M5A and M5B
Asp Ile Gln Leu Thr Gln Ser Pro Ser Ser Leu

Ser Ala Ser Val Gly Asp Arg Val Thr Ile Thr

Cys Arg Ala Gly Glu Ser Val Asp Ile Phe Gly

Val Gly Phe Leu His Trp Tyr Gln Gln Lys Pro

Gly Lys Ala Pro Lys Leu Leu Ile Tyr Arg Ala

Ser Asn Leu Glu Ser Gly Val Pro Ser Arg Phe

Ser Gly Ser Gly Ser Arg Thr Asp Phe Thr Leu

Thr Ile Ser Ser Leu Gln Pro Glu Asp Phe Ala

Thr Tyr Tyr Cys Gln Gln Thr Asn Glu Asp Pro

Tyr Thr Phe Gly Gln Gly Thr Lys Val Glu Ile

Lys
```

-continued

SEQ ID NO: 9 = variable heavy chain domain of M5A

Glu Val Gln Leu Val Glu Ser Gly Gly Gly Leu

Val Gln Pro Gly Gly Ser Leu Arg Leu Ser Cys

Ala Ala Ser Gly Phe Asn Ile Lys Asp Thr Tyr

Met His Trp Val Arg Gln Ala Pro Gly Lys Gly

Leu Glu Trp Val Ala Arg Ile Asp Pro Ala Asn

Gly Asn Ser Lys Tyr Ala Asp Ser Val Lys Gly

Arg Phe Thr Ile Ser Ala Asp Thr Ser Lys Asn

Thr Ala Tyr Leu Gln Met Asn Ser Leu Arg Ala

Glu Asp Thr Ala Val Tyr Tyr Cys Ala Pro Phe

Gly Tyr Tyr Val Ser Asp Tyr Ala Met Ala Tyr

Trp Gly Gln Gly Thr Leu Val Thr Val Ser Ser

SEQ ID NO: 10 = variable heavy chain domain of M5B

Glu Val Gln Leu Val Glu Ser Gly Gly Gly Leu

Val Gln Pro Gly Gly Ser Leu Arg Leu Ser Cys

Ala Ala Ser Gly Phe Asn Ile Lys Asp Thr Tyr

Met His Trp Val Arg Gln Ala Pro Gly Lys Gly

Leu Glu Trp Val Ala Arg Ile Asp Pro Ala Asn

Gly Asn Ser Lys Tyr Val Pro Lys Phe Gln Gly

Arg Ala Thr Ile Ser Ala Asp Thr Ser Lys Asn

Thr Ala Tyr Leu Gln Met Asn Ser Leu Arg Ala

Glu Asp Thr Ala Val Tyr Tyr Cys Ala Pro Phe

Gly Tyr Tyr Val Ser Asp Tyr Ala Met Ala Tyr

Trp Gly Gln Gly Thr Leu Val Thr Val Ser Ser

SEQ ID NO: 11 = light chain variable domain of T84.66

Asp Ile Val Leu Thr Gln Ser Pro Ala Ser Leu

Ala Val Ser Leu Gly Gln Arg Ala Thr Met Ser

Cys

Arg Ala Gly Glu Ser Val Asp Ile Phe Gly Val

Gly Phe Leu His Trp Tyr Gln Gln Lys Pro Gly

Gln Pro Pro Lys Leu Leu Ile Tyr Arg Ala Ser

Asn Leu Glu Ser Gly Ile Pro Val Arg Phe Ser

Gly Thr Gly Ser Arg Thr Asp Phe Thr Leu Ile

Ile Asp Pro Val Glu Ala Asp Asp Val Ala Thr

Tyr Tyr Cys Gln Gln Thr Asn Glu Asp Pro Tyr

Thr Phe Gly Gly Gly Thr Lys Leu Glu Ile Lys

SEQ ID NO: 12 = heavy chain variable domain of T84.66

Glu Val Gln Leu Gln Gln Ser Gly Ala Glu Leu

Val Glu Pro Gly Ala Ser Val Lys Leu Ser Cys

Thr Ala Ser Gly Phe Asn Ile Lys Asp Thr Tyr

-continued

Met His Trp Val Lys Gln Arg Pro Glu Gln Gly

Leu Glu Trp Ile Gly Arg Ile Asp Pro Ala Asn

Gly Asn Ser Lys Tyr Val Pro Lys Phe Gln Gly

Lys Ala Thr Ile Thr Ala Asp Thr Ser Ser Asn

Thr Ala Tyr Leu Gln Leu Thr Ser Leu Thr Ser

Glu Asp Thr Ala Val Tyr Tyr Cys Ala Pro Phe

Gly Tyr Tyr Val Ser Asp Tyr Ala Met Ala Tyr

Trp Gly Gln Gly Thr Ser Val Thr Val Ser Ser

REFERENCES

1. Tong, G., et al., Cancer Med, 2018. 7(11): p. 5327-5338.
2. Esteban, J. M., et al., Cancer, 1994. 74(5): p. 1575-83.
3. van Manen, L., et al., Biomarkers, 2020. 25(2): p. 186-193.
4. Grunnet, M. and J. B. Sorensen, Lung Cancer, 2012. 76(2): p. 138-43.
5. Hammarstrom, S., Semin Cancer Biol, 1999. 9(2): p. 67-81.
6. Tong, G., et al., Cancer medicine, 2018. 7(11): p. 5327-5338.
7. Shao, Y., et al., PLOS ONE, 2015. 10(7): p. e0133830.
8. Peltonen, R., et al., Tumour Biol, 2018. 40(1): p. 1010428317752944.
9. Wagener, C., et al., J Immunol, 1983. 130(5): p. 2308-15.
10. Buchegger, F., et al., J Nucl Med, 1995. 36(3): p. 420-9.
11. Goldenberg, D. M., Int J Biol Markers, 1992. 7(3): p. 183-8.
12. Wong, J. Y., et al., J Nucl Med, 1997. 38(12): p. 1951-9.
13. Behr, T. M., et al., J Nucl Med, 1997. 38(6): p. 858-70.
14. Juweid, M. E., et al., J Nucl Med, 1996. 37(9): p. 1504-10.
15. Ychou, M., et al., Clin Cancer Res, 2008. 14(11): p. 3487-93.
16. Akhavan, D., et al., Cancer Biother Radiopharm, 2020. 35(1): p. 10-15.
17. Wong, J. Y., et al., Cancer Biother Radiopharm, 2006. 21(2): p. 88-100.
18. Segal, N. H., et al., Annals of Oncology, 2017. 28: p. v134.
19. Zhang, C., et al., Mol Ther, 2017. 25(5): p. 1248-1258.
20. Kujawski, M., et al., Oncoimmunology, 2020. 9(1): p. 1724052-1724052.
21. Yazaki, P. J., et al., Protein Engineering, Design and Selection, 2004. 17(5): p. 481-489.
22. Morgenstern, A., et al., Curr Radiopharm, 2018. 11(3): p. 200-208.
23. Ferrer, L., et al., Cancer, 2010. 116(4 Suppl): p. 1093-100.
24. Scheinberg, D. A. and M. R. McDevitt, Curr Radiopharm, 2011. 4(4): p. 306-20.
25. Minnix, M., et al., J Nucl Med, 2021. 62(1): p. 55-61.
26. Minnix, M., et al., J Nucl Med, 2021. 62(6): p. 795-801.
27. Clarke, P., et al., Cancer Res, 1998. 58(7): p. 1469-77.
28. Xu, X., et al., Cancer Res, 2000. 60(16): p. 4475-84.
29. Cha, S. E., et al., Oncoimmunology, 2021. 10(1): p. 1899469.
30. Kujawski, M., et al., Oncoimmunology, 2020. 9(1): p. 1724052.
31. Lewis, M. R., A. Raubitschek, and J. E. Shively, Bioconjug Chem, 1994. 5(6): p. 565-76.
32. Minnix, M., et al., J Nucl Med, 2021. 62(1): p. 55-61.
33. Li, L., et al., Bioconjugate chemistry, 2011. 22(4): p. 709-716.

SEQUENCE LISTING

```
Sequence total quantity: 12
SEQ ID NO: 1            moltype = AA  length = 45
FEATURE                 Location/Qualifiers
source                  1..45
                        mol_type = protein
                        organism = Synthetic construct
SEQUENCE: 1
ARGALAGLYG LUSERVALAS PILEPHEGLY VALGLYPHEL EUHIS                   45

SEQ ID NO: 2            moltype = AA  length = 21
FEATURE                 Location/Qualifiers
source                  1..21
                        mol_type = protein
                        organism = Synthetic construct
SEQUENCE: 2
ARGALASERA SNLEUGLUSE R                                             21

SEQ ID NO: 3            moltype = AA  length = 27
FEATURE                 Location/Qualifiers
source                  1..27
                        mol_type = protein
                        organism = Synthetic construct
SEQUENCE: 3
GLNGLNTHRA SNGLUASPPR OTYRTHR                                       27

SEQ ID NO: 4            moltype = AA  length = 15
FEATURE                 Location/Qualifiers
source                  1..15
                        mol_type = protein
                        organism = Synthetic construct
SEQUENCE: 4
ASPTHRTYRM ETHIS                                                    15

SEQ ID NO: 5            moltype = AA  length = 51
FEATURE                 Location/Qualifiers
source                  1..51
                        mol_type = protein
                        organism = Synthetic construct
SEQUENCE: 5
ARGILEASPP ROALAASNGL YASNSERLYS TYRALAASPS ERVALLYSGL Y            51

SEQ ID NO: 6            moltype = AA  length = 36
FEATURE                 Location/Qualifiers
source                  1..36
                        mol_type = protein
                        organism = Synthetic construct
SEQUENCE: 6
PHEGLYTYRT YRVALSERAS PTYRALAMET ALATYR                             36

SEQ ID NO: 7            moltype = AA  length = 51
FEATURE                 Location/Qualifiers
source                  1..51
                        mol_type = protein
                        organism = Synthetic construct
SEQUENCE: 7
ARGILEASPP ROALAASNGL YASNSERLYS TYRVALPROL YSPHEGLNGL Y            51

SEQ ID NO: 8            moltype = AA  length = 333
FEATURE                 Location/Qualifiers
source                  1..333
                        mol_type = protein
                        organism = Synthetic construct
SEQUENCE: 8
ASPILEGLNL EUTHRGLNSE RPROSERSER LEUSERALAS ERVALGLYAS PARGVALTHR  60
ILETHRCYSA RGALAGLYGL USERVALASP ILEPHEGLYV ALGLYPHELE UHISTRPTYR  120
GLNGLNLYSP ROGLYLYSAL APROLYSLEU LEUILETYRA RGALASERAS NLEUGLUSER  180
GLYVALPROS ERARGPHESE RGLYSERGLY SERARGTHRA SPPHETHRLE UTHRILESER  240
SERLEUGLNP ROGLUASPPH EALATHRTYR TYRCYSGLNG LNTHRASNGL UASPPROTYR  300
THRPHEGLYG LNGLYTHRLY SVALGLUILE LYS                                333

SEQ ID NO: 9            moltype = AA  length = 363
FEATURE                 Location/Qualifiers
source                  1..363
```

-continued

```
                        mol_type = protein
                        organism = Synthetic construct
SEQUENCE: 9
GLUVALGLNL EUVALGLUSE RGLYGLYGLY LEUVALGLNP ROGLYGLYSE RLEUARGLEU  60
SERCYSALAA LASERGLYPH EASNILELYS ASPTHRTYRM ETHISTRPVA LARGGLNALA  120
PROGLYLYSG LYLEUGLUTR PVALALAARG ILEASPPROA LAASNGLYAS NSERLYSTYR  180
ALAASPSERV ALLYSGLYAR GPHETHRILE SERALAASPT HRSERLYSAS NTHRALATYR  240
LEUGLNMETA SNSERLEUAR GALAGLUASP THRALAVALT YRTYRCYSAL APROPHEGLY  300
TYRTYRVALS ERASPTYRAL AMETALATYR TRPGLYGLNG LYTHRLEUVA LTHRVALSER  360
SER                                                                363

SEQ ID NO: 10           moltype = AA  length = 363
FEATURE                 Location/Qualifiers
source                  1..363
                        mol_type = protein
                        organism = Synthetic construct
SEQUENCE: 10
GLUVALGLNL EUVALGLUSE RGLYGLYGLY LEUVALGLNP ROGLYGLYSE RLEUARGLEU  60
SERCYSALAA LASERGLYPH EASNILELYS ASPTHRTYRM ETHISTRPVA LARGGLNALA  120
PROGLYLYSG LYLEUGLUTR PVALALAARG ILEASPPROA LAASNGLYAS NSERLYSTYR  180
VALPROLYSP HEGLNGLYAR GALATHRILE SERALAASPT HRSERLYSAS NTHRALATYR  240
LEUGLNMETA SNSERLEUAR GALAGLUASP THRALAVALT YRTYRCYSAL APROPHEGLY  300
TYRTYRVALS ERASPTYRAL AMETALATYR TRPGLYGLNG LYTHRLEUVA LTHRVALSER  360
SER                                                                363

SEQ ID NO: 11           moltype = AA  length = 333
FEATURE                 Location/Qualifiers
source                  1..333
                        mol_type = protein
                        organism = Synthetic construct
SEQUENCE: 11
ASPILEVALL EUTHRGLNSE RPROALASER LEUALAVALS ERLEUGLYGL NARGALATHR  60
METSERCYSA RGALAGLYGL USERVALASP ILEPHEGLYV ALGLYPHELE UHISTRPTYR  120
GLNGLNLYSP ROGLYGLNPR OPROLYSLEU LEUILETYRA RGALASERAS NLEUGLUSER  180
GLYILEPROV ALARGPHESE RGLYTHRGLY SERARGTHRA SPPHETHRLE UILEILEASP  240
PROVALGLUA LAASPASPVA LALATHRTYR TYRCYSGLNG LNTHRASNGL UASPPROTYR  300
THRPHEGLYG LYGLYTHRLY SLEUGLUILE LYS                               333

SEQ ID NO: 12           moltype = AA  length = 363
FEATURE                 Location/Qualifiers
source                  1..363
                        mol_type = protein
                        organism = Synthetic construct
SEQUENCE: 12
GLUVALGLNL EUGLNGLNSE RGLYALAGLU LEUVALGLUP ROGLYALASE RVALLYSLEU  60
SERCYSTHRA LASERGLYPH EASNILELYS ASPTHRTYRM ETHISTRPVA LLYSGLNARG  120
PROGLUGLNG LYLEUGLUTR PILEGLYARG ILEASPPROA LAASNGLYAS NSERLYSTYR  180
VALPROLYSP HEGLNGLYLY SALATHRILE THRALAASPT HRSERSERAS NTHRALATYR  240
LEUGLNLEUT HRSERLEUTH RSERGLUASP THRALAVALT YRTYRCYSAL APROPHEGLY  300
TYRTYRVALS ERASPTYRAL AMETALATYR TRPGLYGLNG LYTHRSERVA LTHRVALSER  360
SER                                                                363
```

What is claimed is:

1. A humanized anti-carcinoembryonic antigen (CEA) antibody, wherein the humanized anti-CEA antibody is bonded to an alpha-emitting radionuclide; wherein the humanized anti-CEA antibody has a CDR-L1 as set forth in SEQ ID NO:1, a CDR-L2 as set forth in SEQ ID NO:2, a CDR-L3 as set forth in SEQ ID NO:3, a CDR-H1 as set forth in SEQ ID NO:4, a CDR-H2 as set forth in SEQ ID NO:5 or SEQ ID NO:7, and a CDR-H3 as set forth in SEQ ID NO:6.

2. The humanized anti-CEA antibody of claim 1, wherein the humanized anti-CEA antibody has a variable light chain domain of SEQ ID NO:8 and a variable heavy chain domain of SEQ ID NO:9.

3. The humanized anti-CEA antibody of claim 1, wherein the humanized anti-CEA antibody has a variable light chain domain of SEQ ID NO:8 and a variable heavy chain domain of SEQ ID NO:10.

4. The humanized anti-CEA antibody of claim 1, wherein the humanized anti-CEA antibody has a CDR-L1 as set forth in SEQ ID NO:1, a CDR-L2 as set forth in SEQ ID NO:2, a CDR-L3 as set forth in SEQ ID NO:3, a CDR-H1 as set forth in SEQ ID NO:4, a CDR-H2 as set forth in SEQ ID NO:5, and a CDR-H3 as set forth in SEQ ID NO:6.

5. The humanized anti-CEA antibody of claim 1, wherein the alpha-emitting radionuclide is an isotope of actinium, an isotope of lead, an isotope of astatine, an isotope of thorium, an isotope of bismuth, an isotope of radium, an isotope of terbium, or an isotope of uranium.

6. The humanized anti-CEA antibody of claim 1, wherein the alpha-emitting radionuclide is s $^{225}$Ac, $^{212}$Pb, $^{210}$At, $^{211}$At, $^{226}$Th, $^{227}$Th, $^{212}$Bi, $^{213}$Bi, $^{223}$Ra, $^{224}$Ra, $^{149}$Tb, or $^{230}$U.

7. The humanized anti-CEA antibody of claim 1, wherein the alpha-emitting radionuclide is $^{225}$Ac.

8. The humanized anti-CEA antibody of claim 1, wherein the alpha-emitting radionuclide is complexed with a chelating agent; and wherein the chelating agent is covalently bonded to the humanized anti-CEA antibody.

9. The humanized anti-CEA antibody of claim 8, wherein the chelating agent is DOTA, DOTA-2py, DOTA-3py, C-DOTA, PA-DOTA, DODASA, lys-DOTA, C-NOTA, NODASA, N-NOTA, TETA, 2C-TETA, 6C-TETA, BF-PEPA, BF-HEHA, DTPA, ca-DTPA, ibca-DTPA, 1B4M-DTPA, lys-DTPA, vinyl DTPA, glu-DTPA, EDTA, HEHA, macropa, py4pa, crown, bispa$^2$, CHXoctapa, Noneunpa, TCMC, Me-3,2-HOPA, macrocylic tetraphthalimide, CHX-A"-DTPA, $L^{Py}$, DOTP, 3p-C-NETA, or 3p-C-DEPA.

10. The humanized anti-CEA antibody of claim 8, wherein the chelating agent is DOTA, HEHA, macropa, py4pa, crown, bispa$^2$, CHXoctapa, or Noneunpa.

11. The humanized anti-CEA antibody of claim 8, wherein the chelating agent is DOTA.

12. The humanized anti-CEA antibody of claim 1, wherein the humanized anti-CEA antibody has a variable light chain domain of SEQ ID NO:8 and a variable heavy chain domain of SEQ ID NO:9; wherein the alpha-emitting radionuclide is $^{225}$Ac; wherein the alpha-emitting radionuclide is complexed with a chelating agent; wherein the chelating agent is DOTA; and wherein the chelating agent is covalently bonded to the humanized anti-CEA antibody.

13. A method of treating cancer in a subject in need thereof, the method comprising administering to the subject an effective amount of:

(i) the humanized anti-CEA antibody of claim 1, and (ii) an immunocytokine comprising a second anti-carcinoembryonic antigen (CEA) antibody covalently bonded to a cytokine;

wherein (ii) is administered to the subject after (i) is administered to the subject.

14. The method of claim 13, wherein the cytokine is IL-2, IL-4, IL-7, IL-9, IL-12, IL-15, IL-21, IL-33, TNF-α, TGF-β, interferon-γ, or interferon-α.

15. A kit for treating cancer, the kit comprising:

(i) the humanized anti-carcinoembryonic antigen (CEA) antibody of claim 1;

(ii) an immunocytokine comprising a second anti-CEA antibody covalently bonded to a cytokine; and (iii) instructions for use.

16. A method of treating cancer in a subject in need thereof, the method comprising administering to the subject an effective amount of:

(i) a first anti-carcinoembryonic antigen (CEA) antibody bonded to an alpha-emitting radionuclide; wherein the alpha-emitting radionuclide is $^{225}$Ac, $^{212}$Pb, $^{210}$At, $^{211}$At, $^{226}$Th, $^{227}$Th, $^{212}$Bi, $^{213}$Bi, $^{223}$Ra, $^{224}$Ra, $^{149}$Tb, or $^{230}$U, and (ii) an immunocytokine comprising a second anti-carcinoembryonic antigen (CEA) antibody covalently bonded to a cytokine; wherein the cytokine is IL-2, IL-4, IL-7, IL-9, IL-12, IL-15, IL-21, IL-33, TNF-α, TGF-β, interferon-γ, or interferon-α;

wherein the first anti-CEA antibody and the second anti-CEA antibody independently have:

(a) a variable light chain domain of SEQ ID NO:8 and a variable heavy chain domain of SEQ ID NO:9;

(b) a variable light chain domain of SEQ ID NO:8 and a variable heavy chain domain of SEQ ID NO:10; or (c) a variable light chain domain of SEQ ID NO:11 and a variable heavy chain domain of SEQ ID NO:12 wherein the immunocytokine is administered to the subject after the first anti-CEA antibody bonded to the alpha-emitting radionuclide is administered to the subject.

17. The method of claim 16, wherein the first anti-CEA antibody and the second anti-CEA antibody independently have:

(a) the variable light chain domain of SEQ ID NO:8 and the variable heavy chain domain of SEQ ID NO:9; or (b) the variable light chain domain of SEQ ID NO:8 and the variable heavy chain domain of SEQ ID NO:10.

18. The method of claim 16, wherein the alpha-emitting radionuclide is $^{225}$Ac.

19. The method of claim 16, wherein the cytokine is IL-2.

20. The method of claim 16, wherein the cancer is colon cancer or breast cancer.

* * * * *